United States Patent [19]

Takayanagi et al.

[11] Patent Number: 5,166,373
[45] Date of Patent: Nov. 24, 1992

[54] ACYCLIC TERPENES

[75] Inventors: Hisao Takayanagi; Yasunori Kitano, both of Yokohama; Yasuhiro Morinaka, Tsuchiura, all of Japan

[73] Assignee: Mitsubishi Kasei Corporation, Tokyo, Japan

[21] Appl. No.: 815,623

[22] Filed: Dec. 30, 1991

Related U.S. Application Data

[63] Continuation of Ser. No. 640,732, Jan. 16, 1991, abandoned.

[30] Foreign Application Priority Data

| Jan. 17, 1990 | [JP] | Japan | 2-7614 |
| Jan. 17, 1990 | [JP] | Japan | 2-7615 |
| Jun. 27, 1990 | [JP] | Japan | 2-170785 |
| Oct. 25, 1990 | [JP] | Japan | 2-289773 |

[51] Int. Cl.$^5$ ............... C07D 303/32; C07D 303/42; C07D 303/46; C07D 303/16; C07C 47/21; C07C 55/07/69/003; C07C 69/587

[52] U.S. Cl. .................. 549/551; 546/246; 546/248; 549/554; 549/561; 558/55; 558/430; 558/451; 558/452; 558/460; 558/462; 560/15; 560/113; 560/149; 560/152; 560/172; 560/174; 560/183; 560/205; 560/219; 568/415; 568/423; 568/448; 568/495; 568/496; 568/821

[58] Field of Search ............ 549/551, 554, 561; 546/246, 248; 558/55, 430, 451, 452, 460, 462; 560/15, 113, 149, 152, 172, 174, 183, 205, 219, 415, 423, 448, 495, 496; 568/415, 423, 448, 495, 496

[56] References Cited

U.S. PATENT DOCUMENTS

| 3,904,763 | 9/1975 | Bowers | 549/554 |
| 4,460,786 | 7/1984 | Morel | 560/174 |
| 4,693,849 | 9/1987 | Mignani | 560/205 |
| 4,902,334 | 2/1990 | Azuma et al. | 560/183 |

FOREIGN PATENT DOCUMENTS

| 0408053A2 | 1/1991 | European Pat. Off. |  |
| 1814873 | 7/1969 | Fed. Rep. of Germany | 549/561 |

OTHER PUBLICATIONS

Takayanagi et al., Chemical Abstracts, vol. 113, No. 25, 1990, 231 718h.

McMurry et al., Chemical Abstracts, vol. 112, No. 1, 1990, 7 748q.

*Primary Examiner*—Joseph E. Evans
*Attorney, Agent, or Firm*—Wenderoth, Lind & Ponack

[57] ABSTRACT

The present invention provides novel acyclic terpenes of the formula:

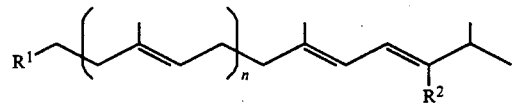

which are useful as intermediates for the industrially advantageous production of sarcophytol A.

1 Claim, No Drawings

ACYCLIC TERPENES

This application is a continuation of now abandoned application, Ser. No. 640,732 filed Jan. 16, 1991, abandoned.

The present invention relates to novel acyclic terpenes. More particularly, the present invention is directed to acyclic terpenes which are useful as intermediates for production of sarcophytol A having anti-carcinogenic promotor activity [Cancer Surveys, 2, 540 (1983); Taisha, Vol. 25, Special Edition, Gan '88,3 (1988)] and anti-tumor activity [Japanese Patent Publication 20213/1988].

The sarcophytol A of the following structure is a cembrane type diterpene-alcohol containing one conjugated double bond and another two double bonds in the 14-membered ring.

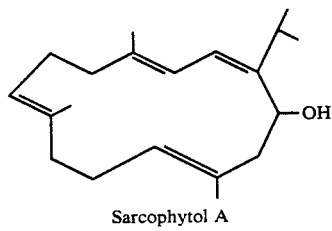

Sarcophytol A

No synthetic method of sarcophytol A has heretofore been known, but the present inventors have proposed a synthetic route of sarcophytol A starting from the sesquiterpenoid as shown below through a formyl compound, Compound F, as a key intermediate [JP Patent Appln. 181710/1989]. The synthetic route is shown below.

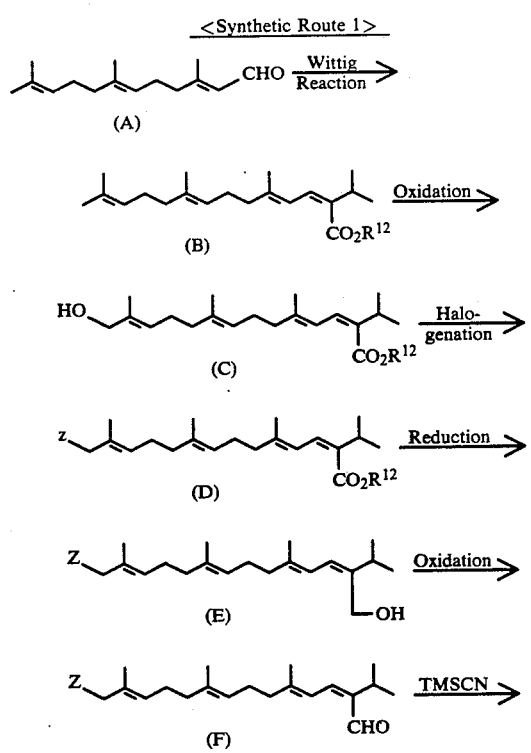

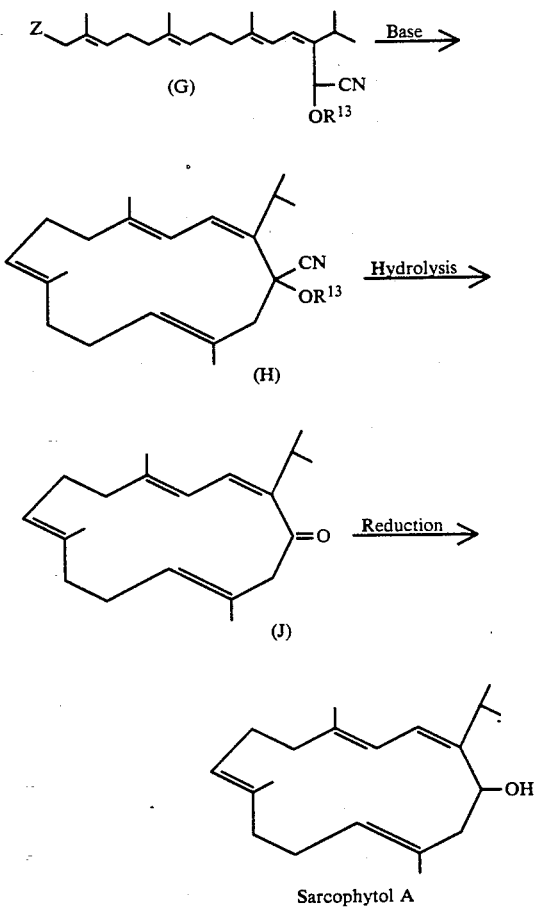

In the above schema, $R^{12}$ is $C_1$-$C_4$ lower alkyl group, $R^{13}$ is trimethylsilyl group, 1-ethoxyethyl group or hydrogen atom and Z is halogen atom such as chlorine atom or bromine atom.

Industrial production of sarcophytol A according to the synthetic route 1 above has a big problem of inevitable oxidation of the terminal methyl group which requires the use of a highly toxic selenium compound and which is poor in the yield and selectivity.

As the result of various investigations for providing sarcophytol A less expensively in a large scale by any industrially more effective process, the present inventors have found that acyclic terpenes of the present invention are very useful as intermediates in the production of sarcophytol A and that the above problem can be solved by the use of the intermediates.

Thus, the present invention provides acyclic terpenes of the formula:

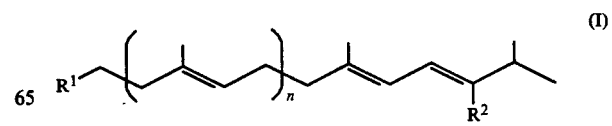

[wherein $R^1$ is

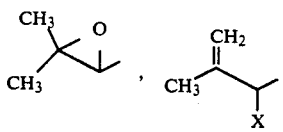

(X is hydroxy group, chlorine atom, —OC(O)R³ (R³ is hydrogen atom, C₁-C₄ alkyl group or optionally substituted phenyl group), —SR⁴, —S(O)R⁴ (R⁴ is C₁-C₄ alkyl group or optionally substituted phenyl group), —NR⁵R⁶, or —N(O)R⁵R⁶ (R⁵ and R⁶ are independently C₁-C₄ alkyl group or taken together form an alkylene ring)),

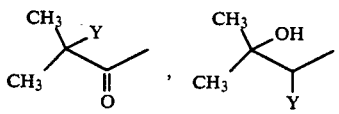

(Y is halogen atom),

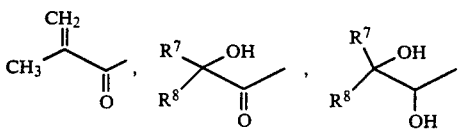

(R⁷ and R⁸ are independently C₁-C₄ alkyl group or taken together form an alkylene ring),

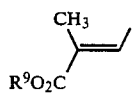

(R⁹ is C₁-C₄ alkyl group),

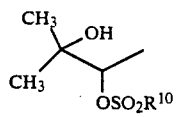

(R¹⁰ is C₁-C₄ alkyl group optionally substituted by halogen atom or optionally substituted phenyl group), or formyl group; R² is cyano group, formyl group or CO₂R¹¹ (R¹¹ is C₁-C₄ alkyl group); and n is 0 or 1 with the proviso that when n is 0, R¹ must be

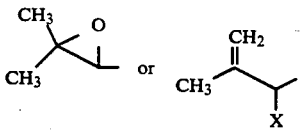

in which X is hydroxy group, chlorine atom or —OC(O)R³].

The present invention will be hereafter explained in detail.

The symbols, R³ and R⁴, in the general formula (I) above illustratively include methyl group, ethyl group, n-propyl group, isopropyl group, n-butyl group, sec-butyl group, tert-butyl group, phenyl group, p-tolyl group, o-nitrophenyl group, etc.. R⁵, R⁶, R⁷ and R⁸ illustratively include methyl group, ethyl group, n-propyl group, isopropyl group, n-butyl group, sec-butyl group, tert-butyl group, or R⁵ and R⁶, or R⁷ and R⁸, each taken together form a ring such as cyclopentyl group, cyclohexyl group or the like. R⁹ and R¹¹ illustratively include methyl group, ethyl group, n-propyl group, isopropyl group, n-butyl group, sec-butyl group, tert-butyl group or the like. R¹⁰ includes methyl group, ethyl group, n-propyl group, isopropyl group, n-butyl group, sec-butyl group, tert-butyl group, trichloromethyl group, trifluoromethyl group, trichloropropyl group, phenyl group, p-tolyl group, o-nitrophenyl group or the like.

Preferred compounds represented by the general formula (I) above are shown below.

(i) When n = 0

(1) When R¹:

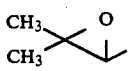

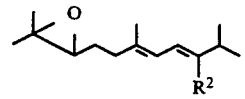

| Compound No. | R² |
|---|---|
| 1 | —CN |
| 2 | —CHO |
| 3 | —CO₂Me |
| 4 | —CO₂Et |
| 5 | —CO₂iPr |
| 6 | —CO₂tBu |

(2) When R¹:

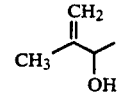

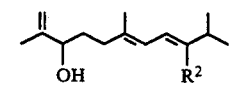

| Compound No. | R² |
|---|---|
| 7 | —CN |
| 8 | —CHO |
| 9 | —CO₂Me |
| 10 | —CO₂Et |
| 11 | —CO₂tBu |

(3) When R¹:

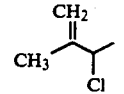

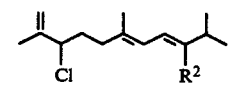

| Compound No. | R² |
|---|---|
| 13 | —CN |
| 14 | —CHO |
| 15 | —CO₂Me |
| 16 | —CO₂Et |

(4) When R¹:

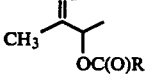

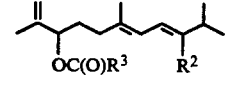

| Compound No. | R² | R³ |
|---|---|---|
| 17 | —CN | —H |
| 18 | —CNO | —CH₃ |
| 19 | —CHO | —CH₃ |

-continued

| | | |
|---|---|---|
| 20 | —CO$_2$Et | —CH$_3$ |
| 21 | —CN | 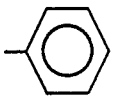 (phenyl) |
| 22 | —CN | 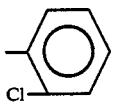 (chlorophenyl) |
| 23 | —CHO | 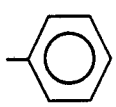 (phenyl) |

(ii) When n = 1

(1) When R$^1$:

| Compound No. | R$_2$ | R$_7$ | R$_8$ |
|---|---|---|---|
| 24 | —CN | CH$_3$ | —CH$_3$ |
| 25 | —CHO | —CH$_3$ | —CH$_3$ |
| 26 | —CO$_2$CH$_3$ | CH$_3$ | —CH$_3$ |
| 27 | —CO$_2$CH$_2$CH$_3$ | —CH$_3$ | —CH$_3$ |
| 28 | —CN | —CH$_2$CH$_3$ | —CH$_2$CH$_3$ |
| 29 | —CN | —CH$_2$CH$_2$CH$_2$CH$_2$CH$_2$— | |
| 30 | —CHO | —CH$_2$CH$_3$ | —CH$_2$CH$_3$ |
| 31 | CO$_2$CH$_3$ | —CH$_2$CH$_2$CH$_2$CH$_2$CH$_2$— | |

(2) When R$^1$:

| Compound No. | R$^2$ | R$^7$ | R$^8$ |
|---|---|---|---|
| 32 | —CN | —CH$_3$ | —CH$_3$ |
| 33 | —CHO | —CH$_3$ | —CH$_3$ |
| 34 | —CO$_2$CH$_3$ | —CH$_3$ | —CH$_3$ |
| 35 | —CN | —CH$_2$CH$_3$ | —CH$_2$CH$_3$ |
| 36 | —CN | —CH$_2$CH$_2$CH$_2$CH$_2$CH$_2$— | |

(3) When R$^1$: —CHO

| Compound No. | R$^2$ |
|---|---|
| 37 | —CN |
| 38 | —CHO |
| 39 | —CO$_2$CH$_3$ |
| 40 | —CO$_2$CH$_2$CH$_3$ |

(4) When R$^1$:

| Compound No. | R$^2$ | R$^9$ |
|---|---|---|
| 41 | —CN | —CH$_3$ |
| 42 | —CN | —CH$_2$CH$_3$ |
| 43 | —CHO | —CH$_3$ |
| 44 | —CO$_2$tBu | —CH$_3$ |

(5) When R$^1$:

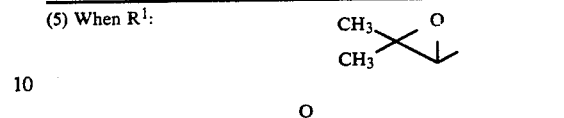

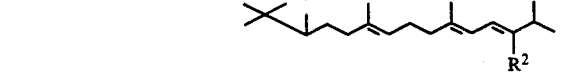

| Compound No. | R$^2$ |
|---|---|
| 45 | —CN |
| 46 | —CHO |
| 47 | —CO$_2$Me |
| 48 | —CO$_2$Et |
| 49 | —CO$_2$iPr |

(6) When R$^1$:

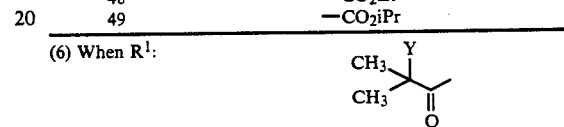

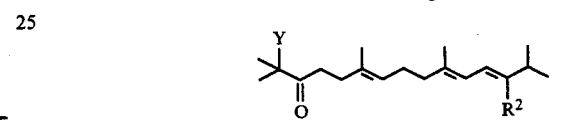

| Compound No. | Y | R$^2$ |
|---|---|---|
| 50 | —Cl | —CN |
| 51 | —Br | —CN |
| 52 | —Br | —CHO |
| 53 | —Cl | —CO$_2$Et |
| 54 | —Br | —CO$_2$Et |

(7) When R$^1$:

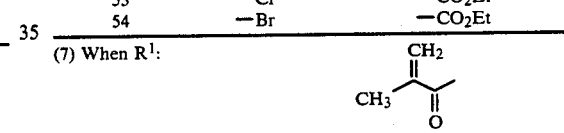

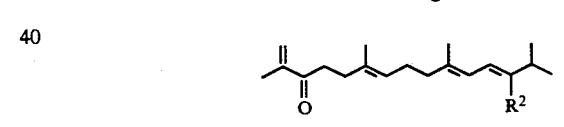

| Compound No. | R$^2$ |
|---|---|
| 55 | —CN |
| 56 | —CHO |
| 57 | —CO$_2$Me |
| 58 | —CO$_2$Et |
| 59 | —CO$_2$iPr |

(8) When R$^1$:

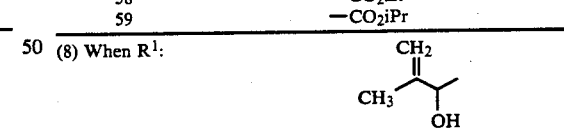

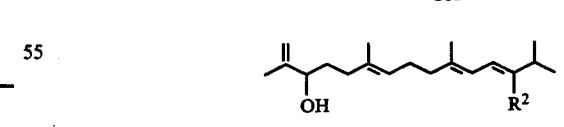

| Compound No. | R$^2$ |
|---|---|
| 60 | —CN |
| 61 | —CHO |
| 62 | —CO$_2$Me |
| 63 | —CO$_2$Et |
| 64 | —CO$_2$iPr |

(9) When R$^1$:

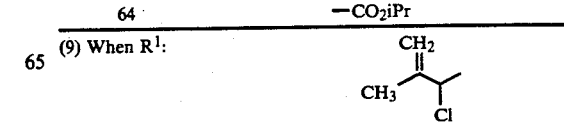

-continued

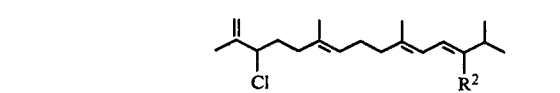

| Compound No. | R² |
|---|---|
| 65 | —CN |
| 66 | —CHO |
| 67 | —CO₂Me |
| 68 | —CO₂Et |

(10) When R¹:

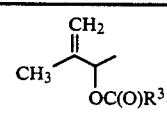

| Compound No. | R² | R³ |
|---|---|---|
| 69 | —CN | —H |
| 70 | —CO₂Et | —H |
| 71 | —CN | —CH₃ |
| 72 | —CHO | —CH₃ |
| 73 | —CO₂Et | —CH₃ |
| 74 | —CN | 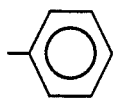 |
| 75 | —CO₂Et | 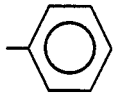 |
| 76 | —CN | 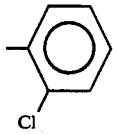 |

(11) When R¹:

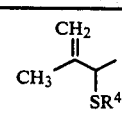

| Compound No. | R² | R⁴ |
|---|---|---|
| 77 | —CN | —CH₃ |
| 78 | —CO₂Et | —CH₃ |
| 79 | —CN | —CH₂CH₃ |
| 80 | —CN | (phenyl) |
| 81 | —CHO | (phenyl) |

-continued

| | |
|---|---|
| 82 | —CO₂Et |

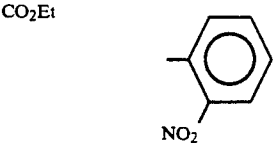

(12) When R¹:

| Compound No. | R² | R⁴ |
|---|---|---|
| 83 | —CN | —CH₃ |
| 84 | —CO₂Et | —CH₃ |
| 85 | —CN | (phenyl) |
| 86 | —CN | (2-nitrophenyl) |

(13) When R¹:

| Compound No. | R² | R⁵ | R⁶ |
|---|---|---|---|
| 87 | —CN | —CH₃ | —CH₃ |
| 88 | —CO₂Et | —CH₃ | —CH₃ |
| 89 | —CN | —CH₂CH₃ | —CH₂CH₃ |
| 90 | —CN | —CH₂CH₂CH₂CH₂CH₂— | |

(14) When R¹:

| Compound No. | R₂ | R₅ | R₆ |
|---|---|---|---|
| 91 | —CN | —CH₃ | —CH₃ |
| 92 | —CO₂Et | —CH₃ | —CH₃ |
| 93 | —CN | —CH₂CH₃ | —CH₂CH₃ |
| 94 | —CN | —CH₂CH₂CH₂CH₂CH₂— | |

(15) When R¹:

| Compound No. | R² | R¹⁰ |
|---|---|---|

-continued

| | | |
|---|---|---|
| 95 | —CN | —CH$_3$ |
| 96 | —CN | —CH$_2$CH$_3$ |
| 97 | —CN | —CCl$_3$ |
| 98 | —CN | 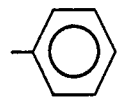 |
| 99 | —CN | 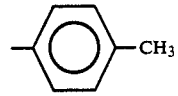 |
| 100 | —CHO | —CH$_3$ |
| 101 | —CHO | —CF$_3$ |
| 102 | —CHO | 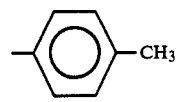 |
| 103 | —CO$_2$CH$_3$ | —CH$_3$ |
| 104 | —CO$_2$CH$_2$CH$_3$ | —CH$_3$ |

-continued

| | | |
|---|---|---|
| 105 | —CO$_2$CH$_2$CH$_3$ | 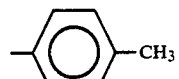 |

(16) When R$^1$: 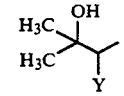

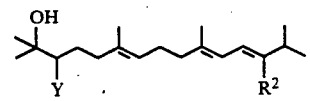

| Compound No. | R$^2$ | Y |
|---|---|---|
| 106 | —CN | —Cl |
| 107 | —CN | —Br |
| 108 | —CN | —I |
| 109 | —CHO | —Cl |
| 110 | —CHO | —Br |
| 111 | —CO$_2$CH$_3$ | —Br |
| 112 | —CO$_2$CH$_2$CH$_3$ | —Cl |
| 113 | —CO$_2$CH$_2$CH$_3$ | —Br |

Production of the compounds of the present invention will be explained below.

The compound (I) can be prepared according to the synthetic route 2 as shown below, starting from, for example monoterpenoid, geranial (Compound K).

<Synthetic Route 2>

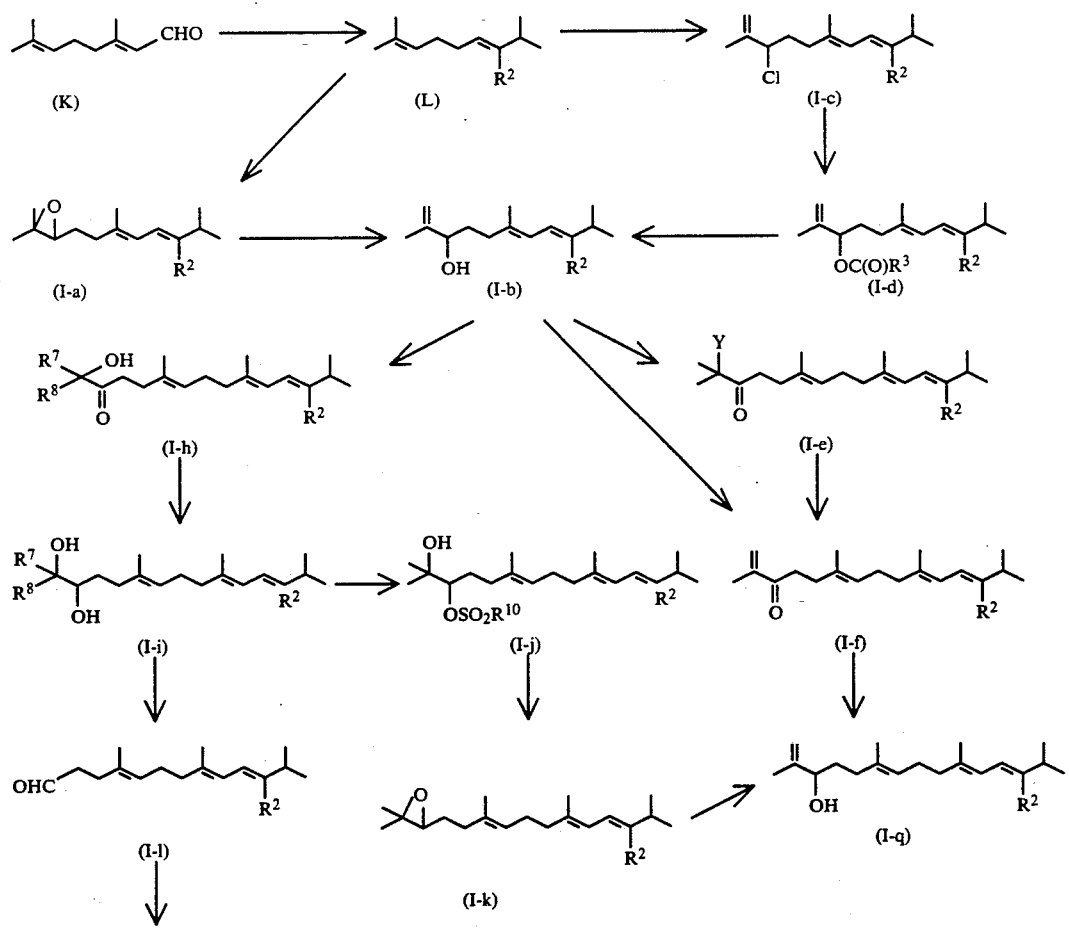

-continued
<Synthetic Route 2>

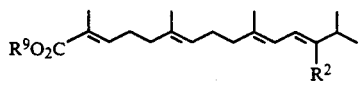

(I-m)

Thus, Compound L wherein R² is cyano group or —CO₂R¹¹ can be prepared by reacting Compound K with 0.1 to 10 mol equivalent of Witting-Horner reagent such as 2-(diethylphosphono)isovaleronitrile, 2-(diethylphosphono)isovaleronitrile, ethyl 2-(diethylphosphono)isovalerate or the like in an ether solvent such as tetrahydrofuran, diethyl ether or the like, a hydrocarbon solvent such as toluene, n-hexane or the like or an aprotic polar solvent such as dimethylformamide, dimethyl sulfoxide or the like at temperature from −100° to 100° C., in the presence of less than 1 mol equivalent (for the Witting-Horner reagent) of a base such as metal hydride (e.g. sodium hydride, potassium hydride), organic metal (e.g. n-butyl-lithium, lithium diisopropylamide) or metal alkoxide (e.g. sodium methoxide, potassium t-butoxide) while allowing to react Compound K with a generated anion, or by reacting Compound K with a phosphorane compound such as

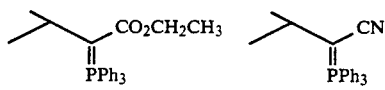

in a halogen solvent such as methylene chloride, chloroform or the like, an ether solvent such as diethyl ether, tetrahydrofuran or the like or an alcohol solvent such as methanol, ethanol or the like at temperature from −50° to 100° C. over a period of 5 minutes to 24 hours. Reaction of the resultant product with 0.1 to 10 mol equivalent of metal hydride such as diisobutylaluminum hydride or the like at temperature from −100° to 150° C. in a hydrocarbon solvent such as n-hexane, heptane, benzene, toluene or the like and subsequent hydrolysis of the resulting product gives Compound L which R² is a formyl group.

Compound I-a can be prepared by reacting compound L (in which R² is cyano group, formyl group or —CO₂R¹¹) with 0.1 to 10 mol equivalent of organic peracid such as peracetic acid, m-chloroperbenzoic acid or the like at −50° to 100° C. in a halogen solvent such as methylene chloride, chloroform or the like, an ester solvent such as ethyl acetate, methyl acetate or the like, or an ether solvent such as diethyl ether, tetrahydrofuran or the like.

Compound I-b can be prepared, for example, by reacting Compound I-a obtained in the said process with 0.1 to 10 mol equivalent of aluminum alkoxide such as aluminum triisopropoxide or the like at temperature from 0° to 150° C. in a hydrocarbon solvent such as toluene, xylene, ligroin or the like or by reacting 0.1 to 10 mol equivalent of a metal amide such as lithium diethylamide, lithium diisopropylamide or the like at temperature from −100° to 100° C. in a solvent such as diethyl ether, tetrahydrofuran or the like.

Further, Compound I-b can also be prepared via Compound I-c which can be prepared by subjecting Compound L to ene-type chlorination [Bull. Chem. Soc. Jpn., 63, 1328 (1990)] wherein Compound L is reacted with 0.1 to 10 mol equivalent of sulfuryl chloride at temperature from −50° to 50° C. in the presence of a base such as sodium carbonate, potassium carbonate or the like in a solvent such as methylene chloride, chloroform or the like. The resultant product I-c is allowed to react with 0.1 to 10 mol equivalent of organic acid metal salt such as sodium formate, sodium benzoate or the like or organic acid ammonium salt such as tetra-n-butylammonium formate, tetra-n-butylammonium acetate, tetra-n-butylammonium benzoate or the like, and if necessary in the presence of crown ether or the like, at temperature from room temperature to 150° C. in an aprotic polar solvent such as dimethylformamide, dimethyl sulfoxide or the like or an ether solvent such as tetrahydrofuran, dimethoxyethane or the like over a period of 30 minutes to 50 hours to give Compound I-d. Compound I-b can be prepared by reacting Compound I-d obtained above with a catalytic amount to 2 mol equivalent of metal alkoxide at temperature from −50° to 50° C. in a solvent such as methanol, ethanol or the like for ester exchanging reaction or by hydrolyzing with 0.5 to 10 mol equivalent of aqueous sodium hydroxide, potassium hydroxide or the like at temperature from −50° to 50° C. in a solvent such as methanol, ethanol, tetrahydrofuran or the like. Compound I-b is allowed to react with 0.1 to 50 mol equivalent of an acetal such as

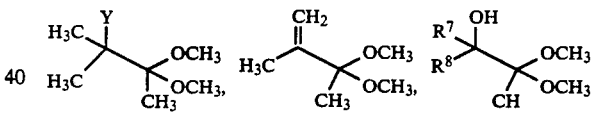

(wherein Y, R⁷ and R⁸ have the same significance as defined above) in the presence of 0.01 to 5 mol equivalent of an acid such as 2,4-dinitrophenol, oxalic acid, o-nitrobenzoic acid or the like at temperature from 100° to 250° C. over a period of 5 minutes to 10 hours for Claisen rearrangement while evaporating the producing methanol to give Compounds I-e, I-f and I-h, respectively.

Further, Compound I-f can be prepared by treating Compound I-e with 0.1 to 50 mol equivalent of a salt such as lithium chloride, lithium carbonate, potassium carbonate or the like or their combination in a solvent such as dimethylformamide, collidine or the like or by treating with an organic base such as pyridine, DBU, DBN or the like.

Compounds I-f and I-h can be converted into Compounds I-g and I-i, respectively by reacting with 0.1 to 10 mol equivalent of a reducing agent such as sodium borohydride, sodium cyanoborohydride or the like at temperature from −80° to 100° C. over a period of 5 minutes to 5 hours in a solvent such as methanol, ethanol or the like.

Moreover, Compound I-i can be converted into Compound I-1 by treating with 0.1 to 10 mol equivalent of periodate such as sodium methaperiodate, potassium methaperiodate or the like at temperature from −50° to 100° C. over a period of from 5 minutes to 5 days in a solvent such as methanol, ethanol or the like. Furthermore, Compound I-i can be converted into Compound I-j by treating with 0.1 to 100 mol equivalent of a sulfonyl halide such as methanesulfonyl chloride, p-toluenesulfonyl chloride or the like or a sulfonic anhydride such as trichloromethanesulfonic anhydride, p-toluenesulfonic anhydride in the presence of 0.1 to 100 mol equivalent of an organic base such as triethylamine, pyridine, N, N-dimethylaniline or the like with or without a halogen solvent such as methylene chloride, chloroform or the like, an ether solvent such as diethyl ether, tetrahydrofuran or the like, or a hydrocarbon solvent such as n-hexane, benzene, toluene or the like, in the latter case the organic base playing a role of solvent, at temperature from $-50°$ to $100°$ C. over a period from 5 minutes to 50 hours.

Compound I-1 can be also prepared by reacting directly Compound I-b with 1 to 100 mol equivalent of alkyl vinyl ether such as ethyl vinyl ether or the like in the presence of 0.1 to 5 mol equivalent of mercury salt such as mercury acetate or the like at temperature form $0°$ to $100°$ C. to give the vinyl ether of Compound I-b or by leading to 3-alkoxyacrylic acid according to a know method [J. Org. Chem., 48, 5406 (1983), followed by heating at temperature from $100°$ to $250°$ C. in the presence of a catalytic amount of hydroquinone or the like in each case.

Compound I-1 can be converted into Compound I-m by reacting 0.1 to 5 mol equivalent of Witting reagent such as carbomethoxyethylidene triphenylphosphorane, carboethoxyethylidene triphenylphosphorane or the like or an anion made from Witting-Horner reagent such as ethyl 2-(diethylphosphono) propionate, ethyl 2-(dimethylphosphono)-propionate or the like at temperature from $-80°$ to $100°$ C. over a period of 5 minutes to 10 hours in an ether solvent such as diethyl ether, tetrahydrofuran or the like, an aprotic polar solvent such as dimethylformamide, dimethyl sulfoxide or the like, a halogen solvent such as methylene chloride, chloroform or the like or an alcohol solvent such as methanol, ethanol or the like.

Compound I-j can be converted into Compound I-k by treating with 0.1 to 100 mol equivalent of a base such as sodium hydroxide, sodium carbonate, potassium carbonate, sodium methoxide, sodium hydride at temperature from $-50°$ to $100°$ C. over a period of 5 minutes to 10 hours in an organic solvent such as methanol, ethanol, acetone, tetrahydrofuran, toluene or the like, and the resultant Compound I-k can be converted into the above-mentioned Compound I-g by treating with 0.1 to 10 mol equivalent of an aluminum alkoxide such as aluminum triisoproxide or the like at temperature from $0°$ to $150°$ C. in a hydrocarbon solvent such as toluene, xylene, ligroin or the like or by treating with 0.1 to 10 mol equivalent of a metal amide such as lithium diethylamide, lithium diisopropylamide or the like at temperature from $-100°$ to $100°$ C. in a solvent such as diethyl ether, tetrahydrofuran or the like.

Further, Compound I can be also prepared from farnesal (Compound M) as shown in the following synthetic route 3.

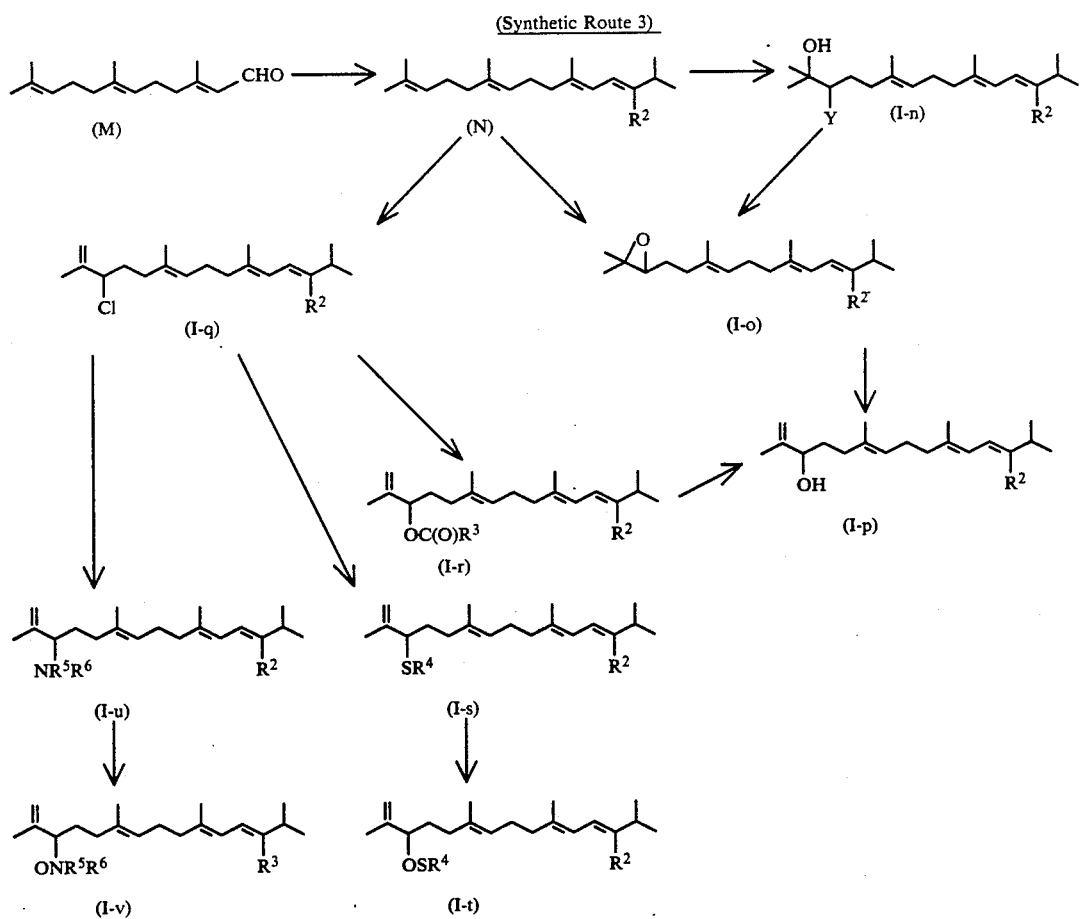

(Synthetic Route 3)

Thus, Compound N can be prepared by subjecting farnesal (Compound M) to the same process as applied to geranial (Compound K) for preparing Compound L. Compounds I-o and I-q can be prepared by the same process as applied to the preparation of Compounds I-a and I-c starting from Compound L. Further, Compound I-o can be prepared by reacting Compound N with 0.1 to 10 mol equivalent of N-halocarbonamide or N-halocarboimide such as N-bromosuccinimide, N-chlorosuccinimide, N-bromoacetamide or the like at temperature from −20° to 100° C. over a period of 5 minutes to 5 hours in aqueous tetrahydrofuran, dioxane or the like and subjecting the resultant Compound I-n to the same process as applied for conversion of Compound I-j to Compound I-k.

Conversion of Compound I-o into Compound I-p and conversion of Compound I-q into Compound I-p via Compound I-r can be attained by the same process as used in the conversions of Compound I-a into Compound I-b and Compound I-c into Compound I-d via Compound I-d vespectively.

Further, Compound I-q can be converted into Compound I-s by reacting with a metal salt of mercaptan such as methanethiol, thiophenol or the like in an aprotic polar solvent such as dimethylformamide, dimethyl sulfoxide or the like, an ether solvent such as tetrahydrofuran, diethyl ether or the like, or an alcohol solvent such as methanol, ethanol or the like at temperature from 0° to 150° C. over a period of 10 minutes to 20 hours, and Compound I-q can also be converted into Compound I-u by reacting with 0.1 to 20 mol equivalent of a secondary amine such as dimethylamine, diethylamine, morpholine or the like at temperature from 0° to 100° C. over a period of 30 minutes to 50 hours in the presence or absence of a solvent such as an alcoholic solvent (e.g. methanol, ethanol) or an aprotic polar solvent (e.g. dimethylformamide, dimethyl sulfoxide).

In case of the absence of a solvent, the amine can work as a solvent. Compound I-s can also be prepared by treating Compound N with 0.1 to 1.5 mol equivalent of a sulfenyl chloride such as phenylsulfenyl chloride, o-chlorophenylsulfenyl chloride or the like at temperature from −50° to 50° C. over a period of 10 minutes to 10 hours and treating with an amine such as triethylamine, pyridine or the like at temperature from 50° to 150° C. in a solvent such as dimethylformamide, toluene or the like [Tetrahedron, 40, 3481 (1984)].

Compound I-s thus obtained can be converted into Compound I-t by reacting with 0.1 to 1.5 mol equivalent of an organic peracid such as peracetic acid, m-chloroperbenzoic acid or the like in a halogen solvent such as methylene chloride, chloroform or the like at −50° to 50° C. over a period of 10 minutes to 10 hours.

Compound I-u can be converted into Compound I-v by treating with an organic peroxide such as hydrogen peroxide, t-butyl hydroperoxide or the like or a periodate such as sodium periodate, potassium periodate or the like at −20° to 100° C. over a period of 10 minutes to 100 hours, and if necessary, in the presence of a metal salt such as tungsten as a catalyst.

Compound F in afore-mentioned Synthetic Route 1 can be prepared from Compound I of the present invention, for example, according to the following Synthetic Route 4.

(Synthetic Route 4)

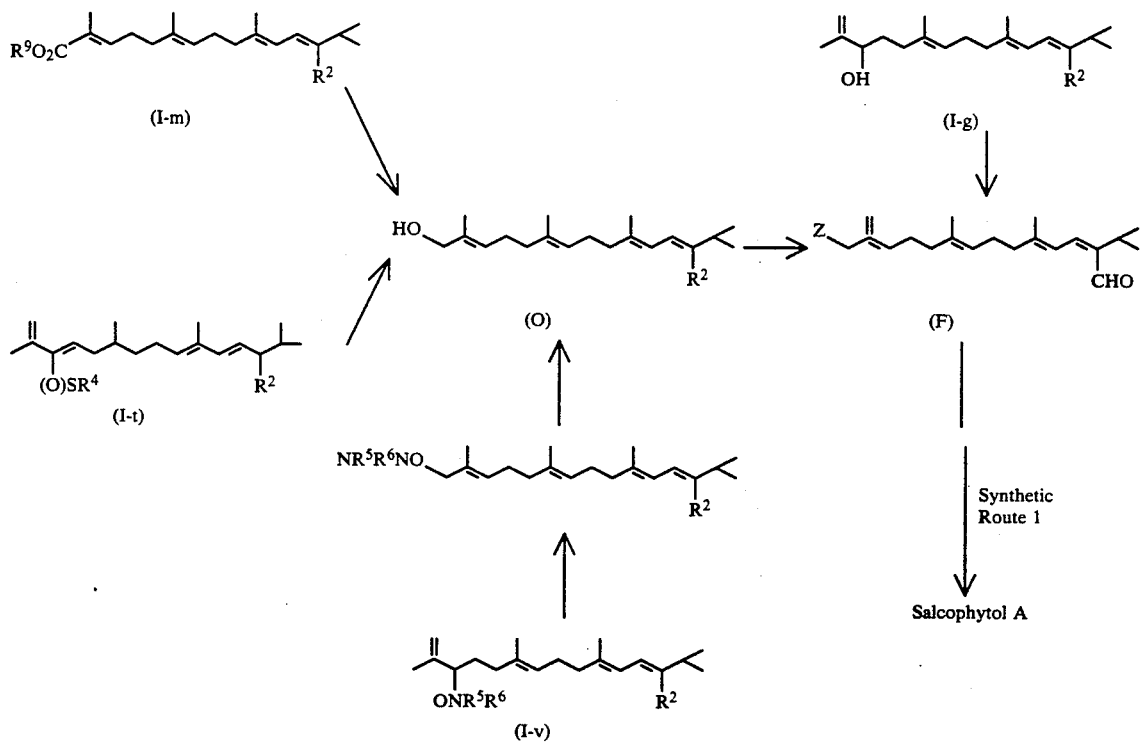

Thus, Compound F is prepared by treating Compound I-g with 0.1 to 100 mol equivalent of a halogenating agent such as thionyl chloride, thionyl bromide, phosphorus trichloride, phosphorus tribromide, hydrogen chloride, hydrogen bromide or the like at temperature of −100° to +100° C. over a period of 5 minutes to 100 hours in an ether solvent such as diethyl ether, tetrahydrofuran, dioxane, diisopropyl ether, dibutyl ether or the like or a hydrocarbon solvent such as n-pentane, n-hexane, cyclohexane or the like and, when $R^2$ is cyano group or —C(O)OR$^{11}$, further treating with 0.1 to 10 mol equivalent of a metal hydride such as diisobutylaluminum hydride or the like or a metal complex such as lithium aluminum hydride or the like at temperature from −100° to 50° C. over a period of 5 minutes to 5 hours in an ether solvent such as diethyl ether, tetrahydrofuran, dimethoxyethane or the like or a hydrocarbon solvent such as benzene, toluene, n-hexane, n-heptane or the like.

Further, Compound 0 can be prepared by reacting Compound I-m with 0.1 to 10 mol equivalent of a metal hydride complex such as lithium aluminum hydride or the like at temperature from −70° to 100° C. in an ether solvent such as diethyl ether, tetrahydrofuran or the like or reacting with 0.1 to 10 mol equivalent of a metal hydride such as diisobutylaluminum hydride or the like at temperature from −70° to 100° C. over a period of 5 minutes to 5 hours in a hydrocarbon solvent such as benzene, toluene, n-hexane, n-pentane or the like; or by reacting Compound I-t with 0.1 to 20 mol equivalent of a trivalent phosphorus compound such as trimethyl phosphite, triethyl phosphite or the like at temperature from 0° to 150° C. over a period of 10 minutes to 100 hours in an appropriate solvent such as methanol, toluene or the like or without solvent; or by heating Compound I-n in the presence or absence of an appropriate solvent such as toluene, acetone or the like at 40° to 100° C. over a period of 10 minutes to 5 hours and then, for example, further reacting with metal zinc at temperature from 0° to 100° C. over a period of 30 minutes to 50 hours in acetic acid [Chemistry Lett., 2035 (1986)].

Compound F can also be prepared from Compound 0 by halogenating the allylic alcoholic without allyl rearrangement; or by reacting with 1.0 to 10 mol equivalent of carbon tetrahalide in the presence of 1.0 to 10 mol equivalent of triphenylphosphine in an inert solvent such as acetonitrile or the like or, in case of chlorination, with carbon tetrachloride without solvent, at temperature from room temperature to 100° C. over a period of 1 to 8 hours; or by reacting with 1.0 to 10 mol equivalent of methanesulfonyl chloride together with a metal halide and s-collidine at temperature from −40° C. to room temperature over a period of 1 to 10 hours and, when $R^2$ is cyano group or —C(O)OR$^{11}$, further treating with 0.1 to 10 mol equivalent of a metal hydride such as diisobutylaluminum hydride or a metal hydride such as lithium aluminum hydride at temperature from −100° to 50° C. over a period of 5 minutes to 5 hours in an ether solvent such as diethyl ether, tetrahydrofuran, dimethoxyethane or the like or a hydrocarbon solvent such as benzene, toluene, n-hexane, n-heptane or the like.

Sarcophytol A can be prepared from Compound F according to Synthetic Route 1.

Thus, Compound G wherein $R^{13}$ is trimethylsilyl group is prepared, for example, by treating Compound F obtained by the above-mentioned process with 1.0 to 10 mol equivalent of trimethylsilylnitrile in the presence of a small amount of a catalyst such as metal cyanide 18-crown-6-ether complex, tetraalkylammonium cyanide or the like at temperature from −20° to 50° C. over a period of 30 minutes to 5 hours with or without solvent such as methylene chloride, chloroform, ethyl acetate or the like. The resultant product can be converted into Compound G wherein $R^{13}$ is hydrogen by treating with 0.1–3N aqueous mineral acid such as hydrochloric acid, sulfuric acid or the like at 0° C. to room temperature over a period of 5 minutes to 5 hours or by treating with a catalytic amount to 10 mol equivalent of tetraalkylammonium salt such as tetrabutylammonium fluoride at temperature from −20° C. to room temperature in a solvent such as tetrahydrofuran, dioxane or the like. Compound G in which $R^{13}$ is 1-ethoxyethyl group can be prepared by reacting Compound G wherein $R^{13}$ is hydrogen with 1.0 to 10 mol equivalent of ethyl vinyl ether in the presence of a catalytic amount of mineral acid such as hydrochloric acid, sulfuric acid or the like, an organic strong acid such as p-toluenesulfonic acid or a salt of strong acid such as p-toluenesulfonic acid pyridinium salt at temperature from −20° C. to room temperature over a period of 30 minutes to 5 hours in a solvent such as ethyl ether, ethyl acetate or the like.

Compound H in which $R^{13}$ is trimethylsilyl group or 1-ethoxyethyl group be prepared by reacting Compound G in which $R^{13}$ is trimethylsilyl group or 1-ethoxycarbonyl group with 1.0 to 10 mol equivalent of a base such as lithium diisopropyamide, lithium bis(trimethylsilyl) amide, sodium hydride or the like at temperature from −70° to 100° C. over a period of 5 minutes to 10 hours in an ether solvent such as ethyl ether, tetrahydrofuran or the like, an aromatic hydrocarbon solvent such as benzene, toluene or the like or a saturated hydrocarbon solvent such as n-hexane, n-heptane or the like. Further, Compound H in which $R^{13}$ is hydrogen atom is prepared by treating it with 0.1–3N aqueous mineral acid such as hydrochloric acid, sulfuric acid or the like at temperature from 0° C. to room temperature over a period of 5 minutes to 5 hours in a solvent such as tetrahydrofuran, methanol or the like or by treating with a catalytic amount to 10 mol equivalent of tetraalkylammonium salt such as tetrabutylammonium fluoride at temperature from −20° C. to room temperature in a solvent such as tetrahydrofuran, dioxane or the like.

The macrocyclic ketone, namely Compound J, can be prepared by treating a solution of Compound H ($R^{13}$ is hydrogen atom) in an organic solvent such as ethyl ether, ethyl acetate or the like with aqueous sodium bicarbonate at temperature from 0° C. to room temperature over a period of 5 minutes to 5 hours, or by treating Compound H ($R^8$ is trimethylsilyl group) with a catalytic amount to 10 mol equivalent of an alkylammonium fluoride such as tetrabutylammonium fluoride in a solvent such as aqueous tetrahydrofuran, dioxane or the like.

Sarcophytol A can be prepared by reacting Compound J thus obtained with 1.0 to 10 mol equivalent of a metal hydride such as diisobutylaluminum hydride or the like or a metal complex such as lithium aluminum hydride or the like at temperature from −70° to 50° C. over a period of 5 minutes to 5 hours in an ether solvent such as ethyl ether, tetrahydrofuran or the like, an aromatic hydrocarbon solvent such as benzene, toluene or the like or a saturated hydrocarbon solvent such as n-hexane, n-heptane or the like.

Further, sarcophytol A in native form shown below is prepared by subjecting Compound J to asymmetric reduction with an asymmetrically modified reducing reagent.

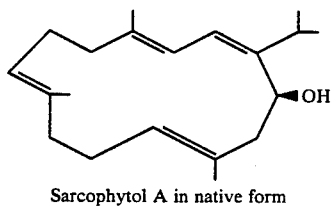

Sarcophytol A in native form

The present invention provides an industrially advantageous synthetic route for preparing sarcophytol A, by providing the compounds of the invention useful as intermediates therefor.

PREPARATION 1

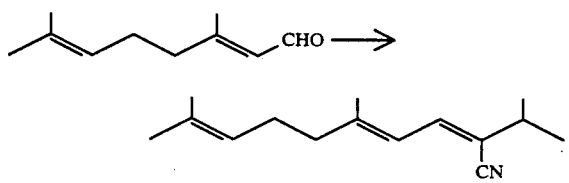

To a solution of 2-(diethylphosphono) isovaleronitrile (6.54 g, 30 mmol) in toluene (55 ml) under argon atmosphere was added 56 ml of a 0.5M solution of potassium bis (trimethylsilyl) amide in toluene on a −70° C. bath with stirring. Half an hour later, geranial (3.80 g, 25 mmol) was added at the same temperature with continuous stirring and the temperature was raised to room temperature in about 10 hours. The reaction mixture was poured into water and separated in two layers. The organic layer was washed with aqueous saturated sodium bicarbonate and saturated brine, dried over anhydrous magnesium sulfate, filtered and concentrated. The resulting residue was chromatographed on a column of silica gel eluting with n-hexane: ethyl acetate (100:1) as an eluent to give the nitrile (4.87 g, 90%, 2Z:2E=22.4:1). 2Z isomer had the following spectra.

IR (film)cm$^{-1}$; 2940, 2890, 2220, 1640, 1450, 1390, 1375, 1295, 1225, 1105, 1030.

NMR (CDCl$_3$, 250 MHz) δppm; 1.17 (d, J=6.8 Hz, 6H CH(CH$_3$)$_2$), 1.61, 1.69 (each bs, each 3H, —C=CCH$_3$), 1.83 (d, J=1.2 Hz, 3H, —C=CCH$_3$), 2.1-2.2 (m, 4H, —CH$_2$CH$_2$—), 2.53 (hep, J=6.8 Hz, 1H, CH(CH$_3$)$_2$), 5.08 (m, 1H, —C=CHCH$_2$—), 6.28, 6.82 (each d, J=11.5 Hz, each 1H, =CH—CH=).

PREPARATION 2

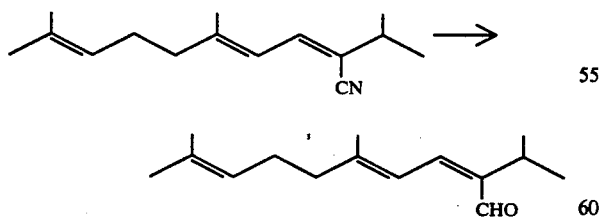

To a solution of the nitrile (2Z, 217 mg, 1 mmol) in 4 ml of n-hexane in argon atmosphere was dropwise added 2 ml of a 1M solution of diisobutylaluminium hydride in toluene under stirring at −70° C. The reaction mixture was kept at the same temperature for 1 hour, mixed with 0.8 ml of water and stirred well after removal of a cooling bath. The resulting white solid was filtered and washed with n-hexane. The filtrate was vigorously stirred with 5 ml of 10% aqueous oxalic acid for 3 hours. The organic layer was separated, washed with water, dried over anhydrous magnesium sulfate, filtered and concentrated. Each procedure above was performed under argon atmosphere. The resulting residue was chromatographed on a column of silica gel eluting with n-hexane: ethyl acetate (50:1) as an eluent to give the objective product (198 mg, 90%).

IR (film)cm$^{-1}$; 2980, 2940, 2880, 1670, 1630, 1455, 1375, 1295, 1135, 1105, 1075.

NMR (CDCl$_3$, 250 MHz)δppm; 1.07 (d, J=6.8 Hz, 6H, —CH(CH$_3$)$_2$), 1.62, 1.69 (each bs, each 3H, —C=CCH$_3$), 1.89 (d, J=1.0 Hz, 3H, —C=CCH$_3$), 2.1-2.3 (m, 4H, —CH$_2$CH$_2$—), 2.91 (hep, J=6.8 Hz, 1H, —CH(CH$_3$)$_2$), 5.10 (m, 1H, =CH=), CH—CH$_2$—), 6.83, 7.14 (each d, J=12.0 Hz, each 1H, =CH—CH=), 10.29 (s, 1H, —CHO).

EXAMPLE 1

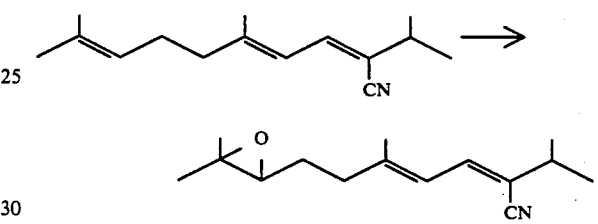

To a solution of the nitrile (2.0 9, 9.2 mmol) in methylene chloride (40 ml) was gradually added m-chloroperbenzoic acid (purity 80%, 2.0 g, 9.3 mmol) on an ice water bath with stirring. The reaction mixture was stirred on an ice water bath for 1 hour and stirred still for 3 hours without the bath. Aqueous saturated sodium bicarbonate was added to the mixture, which was vigorously stirred for half an hour. The organic layer was separated, washed with water, dried and concentrated. The residue was chromatographed on a column of silica gel eluting with n-hexane:ethyl acetate (10:1) as an eluent to give the objective epoxide (2.08 g, 97%).

IR (film)cm$^{-1}$; 2970, 2940, 2880, 2210, 1640, 1460, 1380, 1120, 1025.

NMR (CDCl$_3$, 250 MHz)δppm; 1.17 (d, J=6.8 Hz, 6H, CH(CH$_3$)$_2$), 1.27, 1.32 (each s, each 3H, OC(CH$_3$)$_2$), 1.6-1.8 (m, 2H, =CCH$_2$CH$_2$—), 1.86 (s, 3H, =CCH$_3$), 2.2-2.3 (m, 2H =CCH$_2$CH$_2$—), 2.54 (hep, J=6.8 Hz, 1H, CH(CH$_3$)$_2$), 2.72 (t, J=6.2 Hz, 1H, —CHO—), 6.31 (dd, J=0.9, 11.5 Hz, 1H, =CH—CH=), 6.83 (d, J=11.5 Hz, 1H, =CH—CH=).

EXAMPLE 2

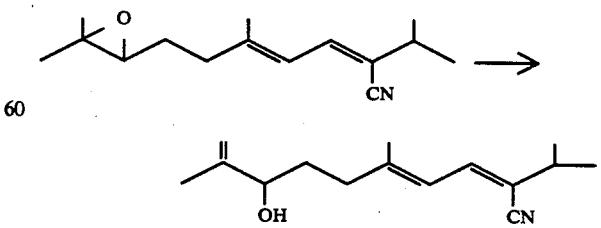

To a solution of the epoxide (1.83 g, 7.85 mmol) in dry toluene (16 ml) was added aluminum triisopropoxide (1.60 g, 7.84 mmol), and the resulting mixture was heated on a 110° C. oil bath under nitrogen atmosphere for 8 hours. After cooling, the reaction mixture was diluted with n-hexane and shaken well with 2N hydrochloric acid. The organic layer was washed with water and saturated aqueous sodium bicarbonate in this order, dried and concentrated. The residue was chromatographed on a column of silica gel, eluting with n-hexane: ethyl acetate (6:1) as an eluent to give the objective allylic alcohol (1.80 g, 98%).

IR (film)cm−1; 3450, 2980, 2950, 2880, 2210, 1640, 1450, 1390, 1295, 1030, 900.

NMR (CDCl3, 250 MHz)δppm; 1.14 (d, J=6.9 Hz, 6H, —CH(CH3)2), 1.6–1.75 (m, 2H, =CCH2CH2), 1.71 (s, 3H, =CCH3), 1.82 (d, J=1.0 Hz, 3H, =CCH3), 2.0–2.3 (m, 2H, =CCH2CH2—), 2.50 (hep, J=6.9 Hz, 1H, —CH(CH3)2) 4.03 (t, J=6.3 Hz, —CHOH). 4.84, 4.94 (each bs, each 1H, C=CH2), 6.27 (dd, J=1.0, 11.5 Hz, =CH—CH=), 6.8 (d, J=11.5 Hz, =CH—CH=).

EXAMPLE 3

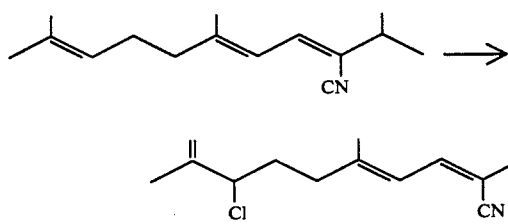

To a solution of the conjugated diene nitrile (431 mg, 1.98 mmol) in methylene chloride (2.1 ml) was added 873 mg of anhydrous sodium carbonate, and the resultant mixture was vigorously stirred on an ice water bath. A solution of sulfuryl chloride (0.17 ml, 2.12 mmol) in methylene chloride (2.1 ml) was gradually added dropwise in 20 minutes to the mixture, which was stirred still for half an hour at the same temperature. The methylene chloride was evaporated under reduced pressure, and the residue was mixed with n-hexane. The mixture was filtered, washed with n-hexane and the filtrate was concentrated. The crude product was chromatographed on a column of silica gel, eluting with n-hexane: ethyl acetate (15:1) as an eluent to give the starting material (34 mg, 7.9%) and the objective secondary allylic chloride (438 mg, 88%).

IR (film)cm−1; 2970, 2940, 2880, 2210, 1635, 1465, 1450, 1390, 1375, 1290, 1030, 905, 875.

NMR (250 MHz, CDCl3)δppm; 1.14 (d, 6H, J=6.8 Hz, —CH(CH3)2), 1.78 (d, 3H, J=1.0 Hz, CH3C=), 1.82 (d, 3H, J=1.1 Hz, CH3C=), 1.8–2.3 (m, 4H, —CH2CH2—), 2.50 (hep, 1H, J=6.8 Hz, —CH(CH3)2), 4.32 (t, 1H, J=7.0 Hz, —CHCl—), 4.90 (m, 1H, HaHbC=), 5.01 (s, 1H, HaHbC=), 6.26 (bd, 1H, J=11.5 Hz, =CH—HC=), 6.78 (dd, 1H, J=11.5, 0.7 Hz, =CH—HC=).

EXAMPLE 4

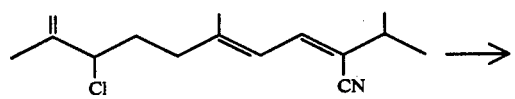

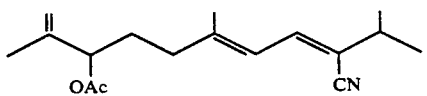

A solution of the allylic chloride (493 mg, 1.96 mmol) and tetrabutylammonium acetate (710 mg, 2.36 mmol) in dimethylformamide (3.0 ml) was heated at 90° C. for 6 hours in argon atmosphere. After completing the reaction, the reaction mixture was poured into ice water and shaken with diethyl ether. The organic layer was washed with water, dried over magnesium sulfate and concentrated. The residue was chromatographed on a column of silica gel for purification to give the objective secondary acetate (480 mg, 89%).

IR (film)cm−1, 2980, 2950, 2880, 2210, 1740, 1635, 1450, 1370, 1295, 1240, 1025, 905.

NMR (250 MHz, CDCl3)δppm; 1.13 (6H, d, J=6.8 Hz, —CH(CH3)2), 1.70 (s, 3H=CCH3), 1.7–1.8 (m, 2H, —C(OAc) CH2—), 1.80 (d, 3H, J=1.0 Hz, =CCH3), 2.04 (S, 3H, OAc), 2.0–2.2 (m, 2H, —C(OAC) CH2CH2—), 2.49 (hep, 1H, J=6.8 Hz —CH(CH3)2), 4.89 (m, 1H =CHaHb), 4.93 (bs, 1H =CHaHb), 5.10 (t, 1H, J=6.7 Hz, —CH(OAc)), 6.23 (dd, 1H, J=11.5, 1.2 Hz, =CH—CH=), 6.78 (dd, 1H, J=11.5, 0.6 Hz, =CH—CH=).

EXAMPLE 5

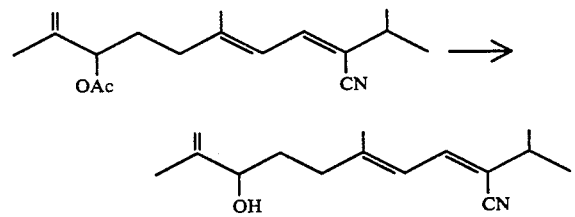

To a solution of the acetate (317 mg, 1.15 mmol) in ethanol (2.0 m) was added 0.6 ml of 2N aqueous sodium hydroxide with stirring on an ice water bath. After the starting material was confirmed to disappear 2 hour later, most of the ethanol was evaporated under reduced pressure. The residue was shaken with water and ether and separated into two layers. The organic layer was dried over magnesium sulfate and concentrated. The residue was chromatographed on a column of silica gel eluting with n-hexane:ethyl acetate (6:1) as an eluent to give the aimed product (263 mg, 98%).

EXAMPLE 6

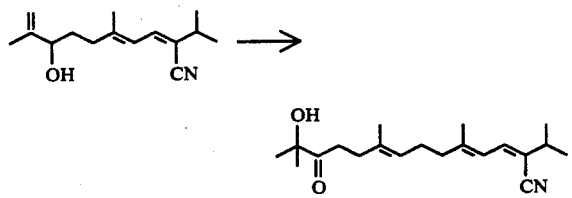

To a mixture of the allylic alcohol (470 mg, 2.02 mmol) and 3, 3-dimethoxy-2-methyl-2-butanol (1.48 g, 10 mmol) was added 2, 4-dinitrophenol (28 mg, 0.15 mmol), and the mixture was heated on a 140° C. oil bath for 5 hours under argon atmosphere. After cooling, the unreacted reagent was evaporated under reduced pressure, and the residue was chromatographed on a column of silica gel eluting with n-hexane: ethyl acetate (6:1) to give the hydroxyketone (609 mg, 95%).

IR (film)cm$^{-1}$; 3520, 2990, 2950, 2890, 2220, 1715, 1640, 1470, 1450, 1370, 1165, 1075, 1025, 965.

NMR (CDCl$_3$, 250 MHz)δppm; 1.14 (d, J=6.8 Hz, 6H, —CH(CH$_3$)$_2$), 1.35 (s, 6H, —C(CH$_3$)$_2$OH), 1.61 (s, 3H, =CCH$_3$), 1.80 (d, J=1.2 Hz, =CCH$_3$), 2.1 (m, 4H, =CCH$_2$CH$_2$C=), 2.26 (bt, J=7.5 Hz, 2H, —CH$_2$CH$_2$-C=O), 2.50 (hep, J=6.8 Hz, 1H, —CH(CH$_3$)$_2$), 2.63 (t, J=7.5 Hz, 2H, —CH$_2$C=O), 5.09 (bm, 1H, =CHCH$_2$—), 6.24 (dd, J=0.8, 11.5 Hz, 1H, =CH—CH=), 6.79 (dd, J=0.7, 11.5 Hz, 1H, =CH—CH=).

EXAMPLE 7

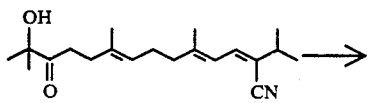

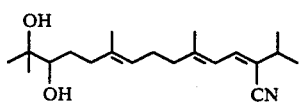

To a solution of the α-hydroxyketone (93.3 mg, 0.29 mmol) in methanol (4 ml) was added 5.5 mg of sodium borohydride on an ice water bath with stirring. The resultant mixture was stirred at the same temperature for 2 hours, and the methanol was evaporated under reduced pressure. The residue was mixed with diethyl ether and water, and the organic layer was washed with water, dried and concentrated. The residue was chromatographed on a column of silica gel eluting with n-hexane: ethyl acetate (3:1 -2:1) as an eluent to give the objective α-diol (81.7 mg, 87%).

IR (film)cm$^{-1}$; 3450, 2970, 2930, 2870, 2210, 1635, 1450, 1385, 1290, 1220, 1160, 1075, 1015, 915.

NMR (CDCl$^3$, 250 MHz)δppm; 1.12, 1.16 (each s, each 3H, C(CH$_3$)$_2$OH), 1.13 (d, J=6.8 Hz, 6H, —CH(CH$_3$)$_2$), 1.3–1.7 (m, 2H, =CCH$_2$CH$_2$CHOH—), 1.59 (d, J=0.6 Hz, 3H, =CCH$_3$), 1.80 (d, J=1.1 Hz, 3H, =CCH$_3$), 2.0–2.3 (m, 6H, =CCH$_2$CH$_2$CHOH, =CCH$_2$CH$_2$C=), 2.49, =(hep, J=6.8 Hz, 1H, —CH(CH$_3$)$_2$), 3.30 (bd, J=10.3 Hz, 1H, —CHOH), 5.13 (bm, 1H, =CHCH$_2$—), 6.23 (dd, J=0.7, 11.5 Hz, 1H, =CH—CH=), 6.79 (dd, J=0.6, 11.5 Hz, 1H, =CH—CH=).

EXAMPLE 8

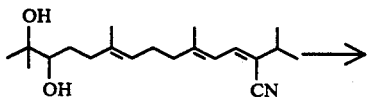

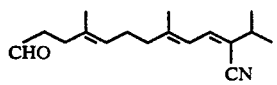

To a solution of the α-diol (503 mg, 1.58 mmol) in methanol (15 ml) was added sodium m-periodate (450 mg, 2.1 mmol), and the resultant mixture was stirred at room temperature for 1 day. The methanol was evaporated under reduced pressure, and the residue was dissolved in diethyl ether and water. The organic layer was washed with water, dried over magnesium sulfate and concentrated. The residue was chromatographed on a column of silica gel eluting with n-hexane:ethyl acetate (10:1) to give the objective aldehyde (348 mg, 85%).

IR (film)cm$^{-1}$; 2970, 2930, 2720, 2200, 1725, 1630, 1440, 1385, 1020.

NMR (CDCl$_3$, 250 NHz)δppm; 1.14 (d, J−6.9 Hz, 6H, —CH(CH$_3$)$_2$), 1.60 (d, J=0.6 Hz, 3H, =CCH$_3$), 1.79 (d, J=1.0 Hz, 3H, =CCH$_2$), 2.14 (m, 4H, =CCH$_2$CH$_2$C=), 2.30 (bt, J=7.4 Hz, 2H, —(CH$_2$CH$_2$-CHO), 2.4–2.6 (m, 3H, —CH$_2$CHO, —CH(CH$_3$)$_2$), 6.23 (d, J=10.2 Hz, 1H, =CH—CH=), 6.79 (dd, J=0.8, 10.2 Hz, 1H, =CH—CH=), 9.72 (t, J=1.8 Hz, 1H, —CHO).

EXAMPLE 9

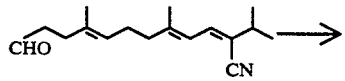

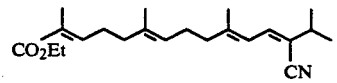

To a solution of the aldehyde (130 mg, 0.5 mmol) in methylene chloride (4 ml) was added (carbethoxyethylidene) triphenylphosphorane (217 mg, 0.6 mmol), and the resultant mixture was stirred at room temperature for 5 hours under argon atmosphere. The methylene chloride was evaporated under reduced pressure, and the residue was chromatographed on a column of silica gel eluting with n-hexane: ethyl acetate as an eluent to give the objective ester (168 mg, 97%).

IR (film)cm$^{-1}$; 2970, 2930, 2880, 2210, 1710, 1640, 1445, 1390, 1365, 1270, 1180, 1120, 1095, 1080, 1025.

NMR (CDCl$_3$, 250 MHz)δppm; 1.14 (d, J=6.8 Hz, 6H, —CH(CH$_3$)$_2$), 1.26 (t, J=7.2 Hz, 3H, —CH$_2$CH$_3$), 1.60 (d, J=0.7 Hz, 3H, =CCH$_3$), 1.805, 1.809 (each s, each 3H, =CCH$_3$), 2.0–2.3 (m, 8H, —CH$_2$CH$_2$—), 2.50 (hep, J=6.8 Hz, 1H, —CH(CH$_3$)$_2$), 4.16 (q, J=7.2 Hz, 2H, —CH$_2$CH$_3$), 5.1 (m, 1H, =CHCH$_2$—), 6.26 (d, J=11.5 Hz, 1H, =CH—CH=), 6.71 (tq, J=7.3, 1.4 Hz, 1H, =CHCH$_2$—), 6.80 (dd, J=0.7, 11.5 Hz, 1H, =CH—CH=).

EXAMPLE 10

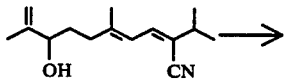

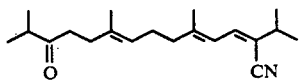

A mixture of the alcohol (320 mg, 1.37 mmol), 3, 3-dimethoxy-2-methylbutene (895 mg, 6.87 mmol) and 2, 4-dinitrophenol (6 mg, 0.04 mmol) was heated with stirring at 110° C. for 8 hours under argon atmosphere while evaporating the generating methanol. After cooling, the unreacted reagents were evaporated, and the residue was chromatographed on a column of silica gel eluting with n-hexane: ethyl acetate (7:1) to give the objective conjugated ketone (262 mg, 64%).

IR (film)cm$^{-1}$; 2980, 2940, 2890, 2215, 1680, 1635, 1450, 1385, 1365, 1085, 1025, 930.

NMR (CDCl$_3$, 250 MHz)δppm; 1.14 (d, d=6.8 Hz, 6H, —CH(CH$_3$)$_2$), 1.60 (s, 3H, =CCH$_3$), 1.80 (d, 3H, J=1.0 Hz, =CCH$_3$), 1.84 (s, 3H, =CCH$_3$), 2.14 (m, 4H, =CCH$_2$CH$_2$C=), 2.25 (bt, J=7.5 Hz, 2H, —CH$_2$CH$_2$-C=O), 2.50 (hep, J=6.8 Hz —CH(CH$_3$)$_2$), 2.75 (t, J=7.5 Hz, 2H, —CH$_2$C=O), 5.08 (bm, 1H, =CH—(CH$_2$)$_2$—), 5.75, 5.95 (each bs, each 1H, —C=CHaHb), 6.24 (bd, J=11.5 Hz, 1H, =CH—CH=), 6.79 (d, J=11.5 Hz, 1H, =CH—CH=).

EXAMPLE 11

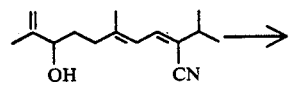

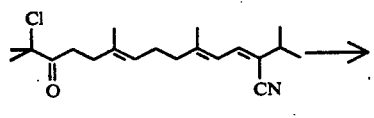

A mixture of the alcohol (316 mg, 1.36 mmol), 2-chloro-3, 3-dimethoxy-2-methylbutane (550 mg, 4.1 mmol) and 2, 4-dinitrophenol (12 mg, 0.065 mmol) was heated with stirring on a 130° C. oil bath for 3 hours under argon atmosphere while evaporating the generating methanol. After cooling, the excessive reagents were evaporated under reduced pressure, and the residue was chromatographed on a column of silica gel eluting with n-hexane:ethyl acetate (7:1) to give the objective α-chloroketone (319 mg, 70%).

IR (film)cm$^{-1}$; 2990, 2950, 2890, 2220, 1720, 1640, 1455, 1385, 1370, 1290, 1120, 1075.

NMR (CDCl$_3$, 250 MHz)δppm; 1.14 (d, J=6.8 Hz, 6H, —CH(CH$_3$)$_2$), 1.61 (s, 3H, =CCH$_3$), 1.65 (s, 6H, —C(CH$_3$)$_2$Cl), 1.80 (s, 3H, =CCH$_3$), 2.14 (m, 4H, =CCH$_2$CH$_2$C=), 2.25 (bt, J=7.7 Hz, 2H, —CH$_2$CH$_2$-C=O), 2.50 (hep, J=6.8 Hz, —CH(CH$_3$)$_2$), 2.83 (t, J=7.7 Hz, 2H, —CH$_2$C=O), 5.11 (bm, 1H, =CH(CH$_2$)$_2$—), 6.25 (bd, J=11.5 Hz, 1H, =CH—CH=), 6.79 (d, J=11.5 Hz, 1H, =CH—CH=).

EXAMPLE 12

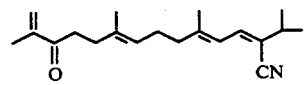

To a solution of the α-chloroketone (319 mg, 0.95 mmol) in dry dimethylformamide (5 ml) were added lithium carbonate (210 mg) and lithium chloride (120 mg), and the resultant mixture was heated with stirring at 110° C. for 6 hours under argon atmosphere. After cooling, the mixture was mixed with water and diethyl ether, and the organic layer was separated, washed with water, dried over magnesium sulfate and concentrated. The residue was chromatographed on a column of silica gel eluting with n-hexane:ethyl acetate (7:1) as an eluent to give the objective conjugated ketone (268 mg, 94%).

EXAMPLE 13

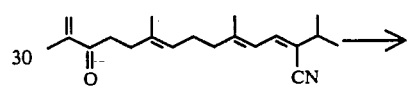

To a solution of the conjugated ketone (417 mg, 1.4 mmol) in methanol was gradually added sodium borohydride (40 mg, 1.1 mmol) with stirring on an ice water bath. About half an hour later, the starting material was confirmed to disappear by TLC, and the methanol was evaporated under reduced pressure. The residue was mixed with diethyl ether and water, and the organic layer was separated, washed with chilled 1N hydrochloric acid, water and saturated aqueous sodium bicarbonate in this order, dried over magnesium sulfate, filtered and concentrated. The residue was chromatographed on a column of silica gel eluting with n-hexane:ethyl acetate (6:1) as an eluent to give the objective alcohol (403 mg, 96%).

IR (film)cm$^{-1}$; 3380, 2990, 2950, 2895, 2220, 1635, 1450, 1390, 1295, 1060, 1025, 900.

NMR (CDCl$_3$, 250 MHz)δppm; 1.14 (d, J=6.8 Hz, 6H, —CH(CH$_3$)$_2$), 1.60 (s, 3H, =CCH$_3$), 1.6–1.7 (m, 2H, —CH (OH) CH$_2$—), 1.70 (s, 3H, =CCH$_3$), 1.81 (d, J=1Hz, 3H, =CCH$_3$), 1.9–2.1 (bm, 2H, —CH(OH) CH$_2$CH$_2$) —), 2.15 (m, 4H, =CCH$_2$CH$_2$C=), 2.50 (hep, 1H, J=6.8 Hz, —CH(CH$_3$)$_2$), 4.01 (bm, —CH (OH)—), 4.81 (m, 1H, —C=CHa Hb), 4.91 (bs, 1H, —C=CHaHb), 5.11 (bm, 1H, =CH—(CH$_2$)$_2$—), 6.25 (bd, J=11.5 Hz, 1H, =CH—CH=), 6.80 (d, J=11.5 Hz, 1H, =CH—CH).

The same alcohol was also obtained in an overall yield of 71% by performing the reaction of Example 10 without isolating the conjugated ketone, namely by evaporating the excessive reagents from the reaction mixture and dissolving the residue in methanol, followed by allowing to react with sodium borohydride

EXAMPLE 14

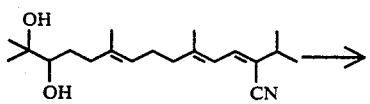

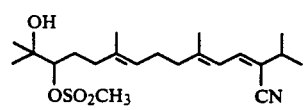

To a solution of the diol (364 mg, 1.14 mmol) and triethylamine (138 mg, 1.37 mmol) in methylene chloride (4 ml) was added methanesulfonyl chloride (143 mg, 1.25 mmol), and the resultant mixture was stirred at room temperature for 1 day. The reaction mixture was poured into ice water, and the organic layer was washed with water, 1N hydrochloric acid, water and saturated aqueous sodium bicarbonate in this order, dried over magnesium sulfate and concentrated. The residue was chromatographed on a column of silica gel eluting with n-hexane:ethyl acetate (5:1) as an eluent to give the objective monomesylate (425 mg, 94%).

IR (film)cm$^{-1}$; 3530, 2980, 2950, 2880, 2210, 1635, 1470, 1450, 1390, 1355, 1340, 1175, 1140, 1030, 975, 940, 925, 915.

NMR (CDCl$_3$, 250 MHz) δppm; 1.13 (d, J=6.8 Hz, 6H, —CH(CH$_3$)$_2$), 1.21, 1.23 (each s, each 3H, —OC(CH$_3$)$_2$), 1.59 (s, 3H, =CCH$_3$), 1.6-1.75 (m, 2H, —OCHCH$_2$—), 1.80 (d, J=1 Hz, 3H, =CCH$_3$), 2.0-2.3 (m, 2H, —OCHCH$_2$CH$_2$—), 2.15 (m, 4H, =CCHCH$_2$C=), 2.50 (hep, J=6.8 Hz, 1H, —CH(CH$_3$)$_2$), 3.10 (s, 3H, —OSO$_2$CH$_3$), 4.53 (dd, J=8.5, 4.0 Hz, 1H, —CHOSO$_2$—), 5.14 (bm, 1H, =CHCH$_2$CH$_2$—), 6.24 (bd, J=11.5 Hz, =CH—CH=), 6.80 (d, J=11.5 Hz, =CH—CH=).

EXAMPLE 15

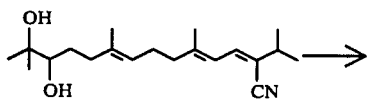

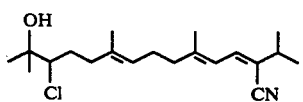

To a solution of the diol (58 mg, 0.18 mmol) in pyridine (0.3 ml) was added p-toluenesulfonyl chloride (42 mg, 0.22 mmol) under ice cooling, and the resultant mixture was stirred at room temperature overnight. The reaction mixture was mixed with ice water and shaken with ether. The organic layer was washed with water, 1N hydrochloric acid, water and saturated aqueous sodium bicarbonate in this order, dried over magnesium sulfate and concentrated. The crude product was chromatographed on a column of silica gel eluting with n-hexane: ethyl acetate (8:1) as an eluent to give the objective chlorohydrin (16 mg, 26%)

IR (film)cm$^{-1}$; 3510, 2990, 2950, 2880, 2210, 1635, 1465, 1450, 1385, 1370, 1340, 1295, 1225, 1175, 1160, 1125, 1030, 970, 915.

NMR (CDCl$_3$, 250 MHz)δppm; 1.14 (d, J=6.8 Hz, 3H, —CH(CH$_3$)$_2$), 1.26, 1.27 (each s, each 3H, OC(CH$_3$)$_2$), 1.59 (s, 3H, =CCH$_3$) 1.6-2.3 (m, 4H, —CHClCH$_2$CH$_2$—), 1.81 (s, 3H, =CCH$_3$), 2.16 (m, 4H, =CCH$_2$CH$_2$C=), 2.50 (hep, J=6.8 Hz, 1H, —CH(CH$_3$)$_2$), 3.75 (dd, J=2.2, 9.3 Hz, 1H, —CHCl—), 5.14 (bm, 1H, =CHCH$_2$CH$_2$—), 6.25 (bd, J=11.5 Hz, 1H, =CH—CH=), 6.80 (d, J=11.5 Hz, 1H, =CH—CH=).

EXAMPLE 16

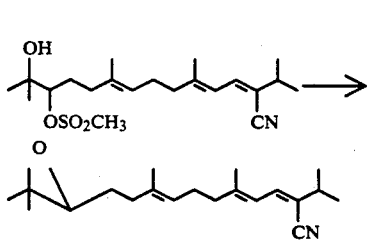

To a solution of the monomesylate (246 mg, 0.62 mmol) in methanol (3 ml) was added anhydrous potassium carbonate (257 mg, 1.9 mmol) on an ice water bath, and the resultant mixture was stirred for 2 hours. The methanol was evaporated under reduced pressure, and the residue was mixed with ice water and shaken with ether. The organic layer was washed with water, dried over magnesium sulfate and concentrated. The crude product was chromatographed on a column of silica gel eluting with n-hexane: ethyl acetate (7:1) as an eluent to give the objective epoxide (172 mg, 92%).

IR (film)cm$^{-1}$; 2980, 2940, 2890, 2220, 1640, 1455, 1380, 1220, 1120, 1025, 900, 875.

NMR (CDCl$_3$, 250 MHz)δppm; 1.13 (d, J=6.8 Hz, 6H, —CH(CH$_3$)$_2$), 1.23, 1.27 (each s, each 3H, OC(CH$_3$)$_2$), 1.5-1.7 (m, 2H, —OCHCH$_2$), 1.60 (d, J=0.6 Hz, =CCH$_3$), 1.80 (d, J=1 Hz, =CCH$_3$), 2.0-2.2 (m, 2H, —OCHCH$_2$CH$_2$—), 2.14 (m, 4H, =CCH$_2$CH$_2$C=), 2.50 (hep, 1H, J=6.8 Hz, —CH(CH$_3$)$_2$), 2.67 (t, J=6.3 Hz, 1H, —CHO—), 5.1 (bm, 1H, =CH —(CH$_2$)$_2$—), 6.24 (bd, J=11.5 Hz, 1H, =CH—CH=), 6.79 (d, J=11.5 Hz, 1H, =CH—CH =).

EXAMPLE 17

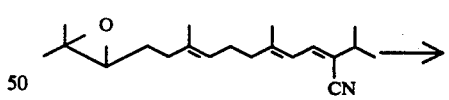

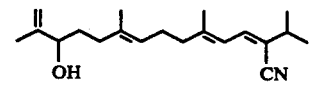

To a solution of the epoxide (186 mg, 0.62 mmol) in toluene (2 ml) was added aluminum triisoproxide (127 mg, 0.62 mmol), and the resultant mixture was stirred at 110° C. for 10 hours under nitrogen atmosphere. After cooling, the reaction mixture was diluted with n-hexane and stirred well with 2N hydrochloric acid. The organic layer was separated, washed with water and saturated aqueous sodium bicarbonate in this order, dried over magnesium sulfate and concentrated. The residue was chromatographed on a column of silica gel eluting with n-hexane: ethyl acetate (6:1) as an eluent to give the objective allylic alcohol (128 mg, 69%).

PREPARATION 3

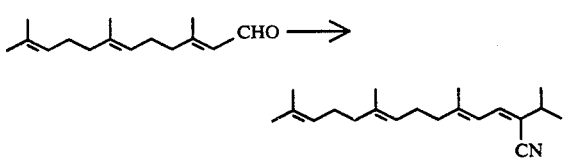

To a solution of 2-(diethylphosphono) isovaleronitrile (8.72 g, 40 mmol) in toluene (75 ml) was gradually added a 0.5M solution of potassium bis (trimethylsillyl) amide in toluene (75 ml) with stirring at −70° C. under argon atmosphere. The resultant mixture was stirred at the same temperature for 30 minutes. To the mixture was added farnesal (5.88 g, 26.7 mmol) with stirring and allowed to warm to room temperature. The reaction mixture was mixed with water, and the organic layer was washed with saturated aqueous sodium bicarbonate and saturated brine, dried over anhydrous magnesium sulfate. After filtration, the filtrate was concentrated and the residue was chromatographed on a column of silica gel eluting with n-hexane:ethyl acetate (100:1) as an eluent to give the objective nitrile (7.23 g, 96%, 2Z:2E=25.6:1). The 2Z compound had the following spectra.

IR (film)cm$^{-1}$; 2980, 2940, 2210, 1640, 1450, 1390, 1290, 1225, 1110, 1030.

NMR (CDCl$_3$, 250 MHz)δppm: 1.14 (d, J=6.8 Hz, 6H, CH(CH$_3$)$_2$), 1.58 (bs, 3H×2, —C=CCH$_3$), 1.65 (bs, 3H, —C=CCH$_3$), 1.81 (d, J=1.2 Hz, 3H, —C=CCH$_3$), 1.9-2.2 (m, 8H, —CH$_2$CH$_2$—×2), 2.50 (hep, J=6.8 Hz, 1H, —CH(CH$_3$)$_2$), 5.06 (m, 1H, =CHCH$_2$—), 6.26, 6.80 (each d, J=11.5z, each 1H, =CH—CH=).

PREPARATION 4

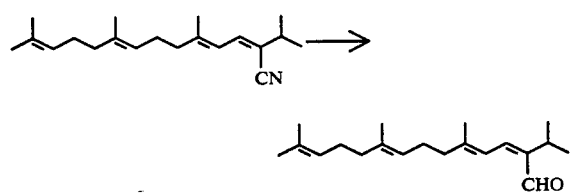

To a solution of the nitrile (856 mg, 3.0 mmol) in n-hexane (30 ml) was added a 0.5M solution of diisobutylaluminum hydride in toluene (6 ml) with stirring at −70° C. under argon atmosphere, and the resultant mixture was mixed with water (3 ml) 1 hour later and stirred well without a cooling bath. The resulting white solid was filtered and washed. The filtrate was concentrated, and the residue was dissolved in n-hexane (10 ml). The solution was mixed with 10% oxalic acid (5 ml) and stirred for 3 hours. The organic layer was extracted and separated, washed with water, dried over anhydrous magnesium sulfate, filtered and concentrated. The residue was chromatographed on a column of silica gel eluting with n-hexane:ethyl acetate (10:1) as an eluent to give the objective aldehyde (865 mg, 84%).

IR (film)cm$^{-1}$; 2980, 2940, 2210, 1640, 1450, 1390, 1290, 1225, 1110, 1030.

NMR (CDCl$_3$, 250MHz)δppm; 1.07 (d, J=6.8 Hz, 6H, —CH(CH$_3$)$_2$), 1.59, 1.61, 1.67 (each bs, 3H×3, —C=CCH$_3$), 1.89 (d, J=1.0 Hz, 3H, —C=CCH$_3$), 2.0-2.2 (m, 8H, —CH$_2$CH$_2$—×2), 2.91 (hep, J=6.8 Hz, 1H, —CH(CH$_3$)$_2$), 5.10 (m, 1H, —C=CCH$_3$), 6.81, 7.16 (each d, J=12.0 Hz, each 1H, =CH—CH=), 10.29 (s, 1H, —CHO).

EXAMPLE 18

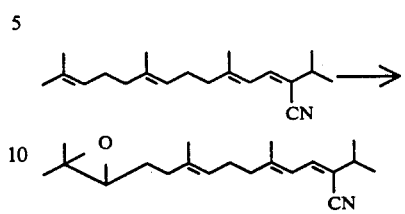

To a solution of the conjugated nitrile (208 mg, 0.73 mmol) in methylene chloride (3 ml) was added m-chloroperbenzoic acid (purity 80%; 165 mg, equivalent to 0.77 mmol) with stirring on an ice water bath. Two hour later, aqueous saturated sodium bicarbonate (2 ml) was added to the mixture, which was stirred well. The organic layer was separated, washed with water, dried over magnesium sulfate and concentrated. The residue was chromatographed on a column of silica gel eluting with n-hexane:ethyl acetate (7:1) as an eluent to give the objective epoxide (165 mg, 75%).

IR (film)cm$^{-1}$; 2980, 2940, 2890, 2220, 1640, 1455, 1380, 1220, 1120, 1025, 900, 875.

NMR (CDCl$_3$, 250 MHz)δppm; 1.13 (d, J=6.8 Hz, 6H, —CH(CH$_3$)$_2$), 1.23, 1.27 (each s, each 3H, OC(CH$_3$)$_2$), 1.5-1.7 (m, 2H, —OCHCH$_2$), 1.60 (d, J=0.6 Hz, =CCH$_3$), 1.80 (d, J=1 Hz, =CCH$_3$), 2.0-2.2 (m, 2H, —OCHCH$_2$CH$_2$—), 2.14 (m, 4H, =CCH$_2$CH$_2$C=), 2.50 (hep, 1H, J=6.8 Hz, —CH(CH$_3$)$_2$), 2.67 (t, J=6.3 Hz, 1H, —CHO—), 5.1 (bm, 1H, =CH—(CH$_2$)$_2$—), 6.24 (bd, J=11.5 Hz, 1H, =CH—CH=), 6.79 (d, J=11.5 Hz, 1H, =CH—CH=).

EXAMPLE 19

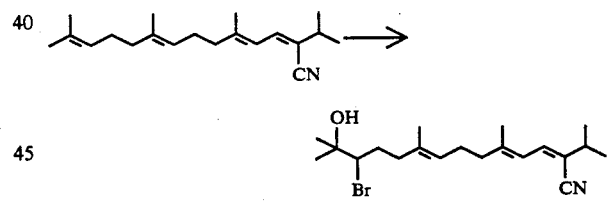

To a solution of the conjugated nitrile (65 mg, 0.23 mmol) in hydrous tetrahydrofuran (THF 1 ml/H$_2$O 0.3 ml) was added N-bromosuccinimide (49 mg, 0.28 mmol) with stirring under ice cooling. Half an hour later, the starting material was confirmed to disappear, and most of the tetrahydrofuran was evaporated under reduced pressure. The residue was extracted with ethyl ether, and the organic layer was washed with water, dried over magnesium sulfate and concentrated. The crude product was chromatographed on a column of silica gel eluting with n-hexane:ethyl acetate (6:1) as an eluent to give the objective bromohydrin (58 mg, 67%).

IR (film)cm$^{-1}$; 3500, 2980, 2950, 2890, 2210, 1635, 1465, 1450, 1385, 1365, 1335, 1200, 1165, 1120, 1025, 965, 905.

NMR (CDCl$_3$, 250 MHz)δppm; 1.13 (d, J=6.8 Hz, 6H, —CH(CH$_3$)$_2$), 1.30, 1.31 (each s, 3H, —OC(CH$_3$)$_2$), 1.58 (s, 3H, =CCH$_3$), 1.7-2.4 (m, 4H, —CHBrCH$_2$CH$_2$—), 1.80 (d, J=1.2 Hz, 3H, =CCH$_3$), 2.15 (m, 4H, =CCH$_2$CH$_2$C=), 2.49 (hep, J=6.8 Hz, 1H, —C$\underline{H}$(CH$_3$)$_2$), 3.92 (dd, J=1.8, 11.2 Hz, 1H, —C$\underline{H}$ Br—), 5.15 (bm, 1H, =C$\underline{H}$CH$_2$CH$_2$—), 6.24 (dd, J=11.5, 1.0 Hz, 1H, —C$\underline{H}$—CH=), 6.79 (d, J=11.5 Hz, 1H, =CH—C$\underline{H}$=).

EXAMPLE 20

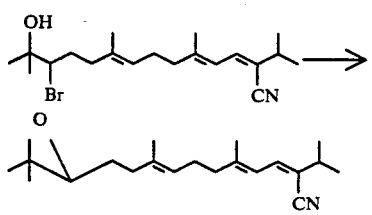

To a solution of the bromohydrin (380 mg, 10 mmol) in methanol (5.0 ml) was added anhydrous potassium carbonate (550 mg, 4.0 mmol), and the resultant mixture was vigorously stirred. The methanol was evaporated under reduced pressure and the residue was mixed with ice water and shaken with ethyl ether. The organic layer was washed with water, dried over magnesium sulfate and concentrated. The crude product was chromatographed on a column of silica gel eluting with n-hexane:ethyl acetate (7:1) as an eluent to give the same epoxide as obtained in the foregoing Example (285 mg, 95%).

EXAMPLE 21

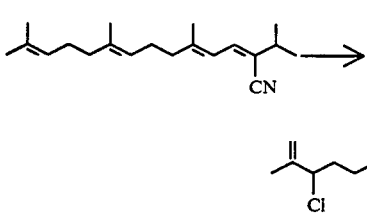

To a suspension of 61% calcium hypochlorite (2.58 g, 11 mol) in saturated aqueous sodium sulfate (7.5 ml) was added a solution of the conjugated nitrile (2.85 g, 10 mmol) in methylene chloride (66 ml), and the resultant mixture was vigorously stirred while adding bit by bit small chips of dry ice (15 g). Insoluble material was filtered off, and the filtrate was separated. The organic layer was dried over magnesium sulfate and concentrated. The residue was chromatographed on a column of silica gel eluting with n-hexane:ethyl acetate (40:1) as an eluent to give the objective chlorine compound (2.69 g, 84%).

IR (film)cm$^{-1}$; 2970, 2930, 2880, 2205, 1635, 1450, 1390, 1375, 1365, 1295, 1225, 1160, 1100, 1025, 905, 875.

'H-NMR(250 MHz, CDCl$_3$)$\delta$ppm: 1.14 (d, bH, J=6.8 Hz, —CH(C$\underline{H}$$_3$)$_2$), 1.59, 1.78 (s, each 3H, =CC$\underline{H}$$_3$), 1.81 (d, 3H, J=1.0 Hz, =CC$\underline{H}$$_3$), 1.8-2.1 (m, 4H —CClCH$_2$C$\underline{H}$$_2$C=), 2.1 (m, 4$\underline{H}$, =CC$\underline{H}$$_2$CH$_2$C=), 2.50 (hep, 1$\underline{H}$, J=6.8 Hz, —C$\underline{H}$(CH$_3$)$_2$), 4.31 (1H, t, J=7.2 Hz, —C$\underline{H}$Cl—), 4.87 (m, 1H HaHbC=), 4.97 (bs, 1H, HaH$\underline{b}$c=), 5.11 (bm, 1H, =C$\underline{H}$CH$_2$—), 6.26 (bd, 1H, J=11.5 Hz, =C$\underline{H}$—CH=), 6.80 (dd, 1H, J=11.5, 0.7 Hz, =CH—C$\underline{H}$=).

EXAMPLE 22

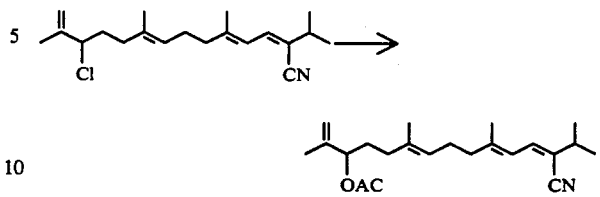

The same reaction as in Example 4 was performed to give the objective secondary ester in a yield of 92%.

IR (film)cm$^{-1}$; 2970, 2930, 2880, 2210, 1740, 1635, 1430, 1370, 1240, 1050, 1025, 910.

NMR (250 MHz, CDCl$_3$)$\delta$ppm: 1.14 (d, 6H, J=6.8 Hz, —CH(C$\underline{H}$$_3$)$_2$), 1.58, 1.69 (s, each 3H, =CC$\underline{H}$$_3$), 1.6-1.8 (m, 2$\underline{H}$, —C(OAc) CH$_2$—), 1.80 (3H d, J=1.0 Hz, =CC$\underline{H}$$_3$), 1.8-2.0 (m, 2$\underline{H}$, —C (OAc) CH$_2$C$\underline{H}$$_3$) 2.02 (s, 3$\underline{H}$ —OAC), 2.1 (m, 4H, =(C$\underline{H}$$_2$CH$_2$C=), 2.50 (hep, 1H, —C$\underline{H}$(CH$_3$)$_2$), 4.86 (m, 1H, =(HaHb), 490 (bs 1H=(HaHb), 5.0-5.2 (m, 2H, =CH$\underline{H}$$_2$—& —C$\underline{H}$ (OAc)—), 6.24 (bd, 1H, J=11.5 Hz, =C$\underline{H}$—CH=), 6.79 (d, 1H, J=11.5 Hz, =CH—C$\underline{H}$ =).

EXAMPLE 23

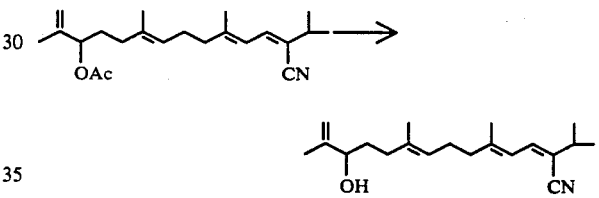

The same reaction as in Example 5 was performed to give the objective alcohol in a yield of 97%.

EXAMPLE 24

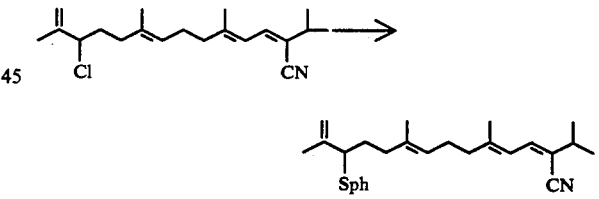

To a suspension of sodium hydride (60%, 30 mg, 0.75 mmol) in dimethylformamide (0.7 ml) was added thiophenol (98 mg, 0.89 mmol) with stirring on an ice water bath under argon atmosphere. The resultant mixture was stirred for about 30 minutes to give a homogeneous solution, which was mixed with the chloride (240 mg, 0.75 mmol) and stirred well. Twenty minutes later, the reaction mixture was mixed with ice water and ether, separated in two layers and the organic layer was dried over magnesium sulfate and concentrated. The residue was chromatographed on a column of silica gel eluting with n-hexane:ethyl acetate (25:1) as an eluent to give the objective sulfide (261 mg, 88%).

IR (film)cm$^{-1}$; 3080, 2970, 2930, 2870, 2205, 1635, 1580, 1435, 1385, 1370, 1290, 1220, 1090, 1070, 1025, 895.

NMR (250 MHz, CDCl$_3$)$\delta$ppm; 1.17 (d, 6H, J=6.8 Hz, —CH(C$\underline{H}$$_3$)$_2$), 1.60, 1.77 (s, each 3H, =CC$\underline{H}$$_3$), 1.7-1.90 (m, 2H, —C(Sph) CH$_2$—), 1.83 (d, 3H, J=1.1 Hz, =CCH$_3$), 2.06 (bt, 2H, J=7.6 Hz, —C(Sph) CH$_2$CH$_2$—), 2.52 (hep, 1H, J=6.8 Hz, —CH(CH$_3$)$_2$), 3.58 (dd, 1H, J=8.4, 6.6 Hz, —CH(Sph)—), 4.61 (bs, 1H, =CHaHb), 4.73 (m, 1H, =CHaHb), 5.11 bm, 1H, =CHCH$_2$—), 6.28 (bd, 1H, J=11.5 Hz, =CH—CH=), 6.81 (1H, d, J=11.5 Hz, =CH—CH=), 7.2-7.4 (m, 5H, —Sph).

EXAMPLE 25

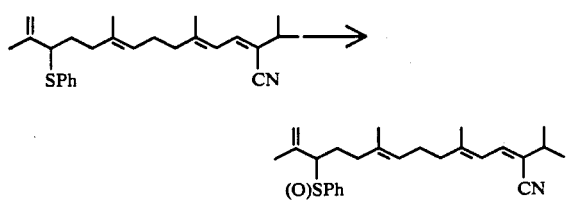

To a solution of the sulfide (255 mg, 0.65 mmol) in methanol (1.5 ml) was added aqueous solution of sodium m-periodate (166 mg, 0.78 mmol), and the resultant mixture was stirred at room temperature for 3 days. The methanol was evaporated under reduced pressure, and the residue was mixed with ether and water. The organic layer was dried over magnesium sulfate and concentrated. The crude product was chromatographed on a column of silica gel eluting with n-hexane:ethyl acetate (7:1) as an eluent to give the objective sulfoxide (200 mg, 74%).

IR (film)cm$^{-1}$; 3070, 2970, 2930, 2880, 2205, 1635, 1585, 1445, 1390, 1305, 1150, 1085, 1025, 910.

NMR 9(250 MHz, CDCl$_3$)δppm; 1.17 (d, 6H, J=6.8 Hz, —CH(CH$_3$)$_2$), 1.54, 1.79, 1.83 (s, each 3H=CCH$_3$), 1.8-2.1 (m, 4H, —C(Sph) CH$_2$CH$_2$—), 2.15 (4H, m=CCH$_2$CH$_2$C), 2.53 (hep, 1H, J=6.8 Hz, —CH(CH$_3$)$_2$), 3.50 (dd, 1H, J=11.0, 3.0 Hz, —CH S(O)ph), 4.70, 5.06 (s, each 1H, =CH$_2$), 5.06 (bm, 1H=CHCH$_2$—), 6.27 (bd, 1H, J=11.5 Hz, =CH—CH=), 6.82 (d, 1H, J=11.5 Hz, =CH—CH=), 7.5-7.9 (m, 5H, —S(O)ph).

EXAMPLE 26

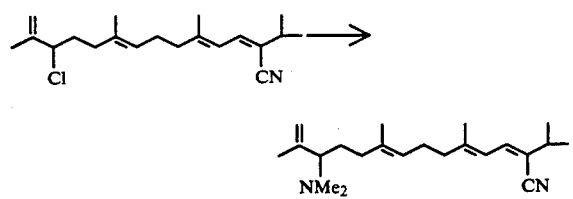

To a solution of the chlorine compound (182 mg, 0.57 mmol) in ethanol (1.5 ml) was added 50% aqueous dimethylamine (0.5 ml), and the resultant mixture was allowed to stand at room temperature for 2 days. The excessive dimethylamine and ethanol were evaporated under reduced pressure, and the residue was mixed with ether and 1N aqueous sodium hydroxide. The organic layer was dried over magnesium sulfate and concentrated. The residue was chromatographed on a column of silica gel eluting with n-hexane:ethyl acetate (1:1) as an eluent to give the objective amine (130 mg, 70%).

IR (film) cm$^{-1}$; 2970, 2950, 2880, 2820, 2780, 2210, 1635, 1465, 1450, 1390, 1365, 1150, 1100, 1045, 1025, 900.

NMR (250 MHz, CDCl$_3$)δppm; 1.16 (d, 6H J=6.8 Hz, —CH(CH$_3$)$_2$, 1.58, 1.63 (s, each 3H, =CCH$_3$), 1.6-2.1 (m, 4H, C(NMe2) CH$_2$CH$_2$—), 1.80 (d, 3H, J=1.0 Hz, =CCH$_3$), 2.15 (m, 4H, =CCH$_3$ 2.17 (s, 6H, —NMe$_2$), 3.36 (dd, 1H, J=10.5, 4.0 Hz, —CH(NMe$_2$)), 2.50 (hep, 1H, J=6.8 Hz, —CH(CH$_3$)$_2$ 4.76 (bs, 1H=CHaHb), 4.84 (m, 1H=CHaHb), 5.05 (bm, H, =CHCH$_2$—), 6.25 (bd, 1H, J=11.5 Hz, =CH—CH=), 6.79 (d, 1H, J=11.5 Hz, =CH—CH=).

EXAMPLE 27

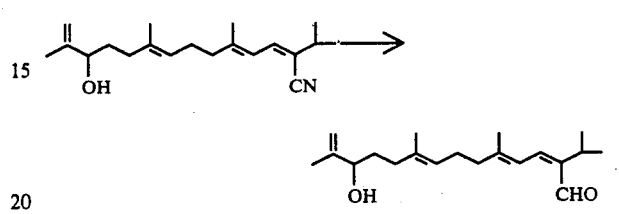

To a solution of the nitrile (218 mg, 0.72 mmol) in n-hexane (5 ml) was dropwise added through a syringe a 0.9M solution of diisobutylaluminium hydride in n-hexane (2.4 ml) on a low temperature (—78° C.) bath under argon atmosphere. After finishing the addition, the refrigerant bath was removed, and the mixture was stirred at room temperature for 3 hours. The mixture was again chilled on a refrigerant bath, mixed with 10% aqueous acetic acid (4 ml) and stirred still for 6 hours on an ice water bath in place of the refrigerant bath. The organic layer was separated, washed with water (twice) and saturated aqueous sodium bicarbonate, dried over magnesium sulfate and concentrated. The residue was chromatographed on a column of silica gel eluting with n-hexane: ethyl acetate (6:1) as an eluent to give the objective aldehyde (152 mg, 69%).

IR (film)cm$^{-1}$; 3450, 2970, 2940, 2880, 1665, 1625, 1450, 1390, 1295, 1230, 1180, 1130, 1100, 1065, 1020, 995, 895.

NMR (CDCl$_3$, 250 MHz)δppm: 1.02 (d, J=7.0 Hz, 6H, —CH(CH$_3$)$_2$), 1.5-1.65 (m, 2H, —C(OH)CH$_2$—), 1.59 (d, J=0.8 Hz, 3H, =CCH$_3$), 1.67 (s, 3H, =CCH$_3$), 1.85 (d, J=1.3 Hz, 3H, =CCH$_3$), 1.99 (bq, J=7.5 Hz, 2H, —C(OH) CH$_2$CH$_2$—), 2.17 (m, 4H, =CCH$_2$CH$_2$C=), 2.86 (hep, J=7.0 Hz, 1H, —CH(CH$_3$)$_2$), 3.98 (bt, J=5.7 Hz, 1H, —CH(OH)—), 4.78, 4.88 (each m, each 1H, —C=CH$_2$), 5.11 (bm, 1H, =CHCH$_2$CH$_2$—), 6.79 (bd, J=12.0 Hz; 1H, =CH—CH=), 1.09 (d, J=12.0 Hz, 1H, =CH—CH=), 10.23 (s, 1H, —CHO).

REFERENCE EXAMPLE 1

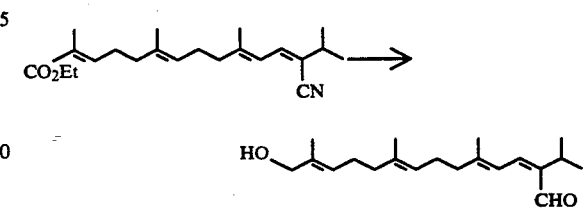

To a solution of the cyanoester (175 mg, 0.51 mmol) in toluene (5 ml) was dropwise added a 1M solution of diisobutylaluminium hydride in toluene (2.1 ml, 2.1 mmol) at —70° C. under argon atmosphere. The resultant mixture was stirred at the same temperature for 2 hours, mixed with aqueous oxalic acid (1M, 4.2 ml), put under argon atmosphere again and allowed to make it to room temperature in about 2 hours while stirring. Completion of the hydrolysis was confirmed by high performance liquid chromatography, and the organic layer was washed with water and saturated aqueous sodium bicarbonate, dried, filtered and concentrated. The residue was chromatographed on a column of silica gel eluting with n-hexane:ethyl acetate (7:1) to give the objective hydroxy-aldehyde (123 mg, 79%).

IR (film)cm$^{-1}$; 3430, 2960, 2920, 2870, 1670, 1630, 1450, 1390, 1295, 1230, 1130, 1070, 1010.

NMR (250 MHz, CDCl$_3$)δppm; 1.04 (6H, d, J=6.8 Hz, —CH(CH$_3$)$_2$), 1.59 (3H, d, J=0.6 Hz, CH$_3$—C=), 1.63 (3H, bs, CH$_3$—C=), 1.86 (3H, d, J=1.2 Hz, CH$_3$—C=), 1.7-2.2 (8H, m, —CH$_2$CH$_2$—), 2.88 (1H, hep, J=6.8 Hz, CH(CH$_3$)$_2$), 3.95 (2H, bs, —CH$_2$OH), 5.09 (1H, m, —CH$_2$CH=), 5.38 (1H, bt, J=6.8 Hz, —CH$_2$CH=), 6.80 (1H, d, J=12.0 Hz, =CH—CH=), 7.11 (1H, d, J=12.0 Hz, =CH—CH=), 10.25 (1H, s, —CHO).

REFERENCE EXAMPLE 2

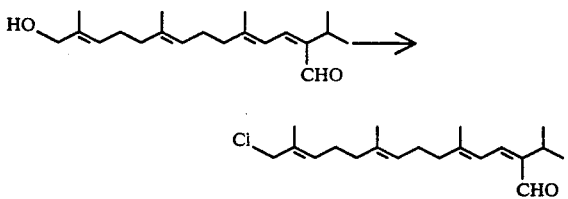

A solution of dry lithium chloride (64 mg, 1.5 mmol), 2, 6-lutidine (0.23 ml, 2.0 mmol) and the starting material (305 mg, 1.0 mmol) in dimethylformamide (1.0 ml) was chilled on an ice water bath and mixed with methanesulfonyl chloride (160 mg, 1.4 mmol) with stirring in argon atmosphere. About 8 hours later, the starting material was confirmed to disappear, and the reaction mixture was dissolved in water and ether. The organic layer was washed with water, dried over magnesium sulfate and concentrated. The residue was chromatographed on a column of silica gel eluting with n-hexane:ethyl acetate as an eluent to give the objective Compound F (281 mg, 87%).

IR (film)cm$^{-1}$; 2970, 2930, 2880, 1670, 1630, 1445, 1390, 1295, 1265, 1135.

NMR (CDCl$_3$, 250 MHz)δppm; 1.04 (d, J=7.0 Hz, 6H, —CH(CH$_3$)$_2$), 1.59, 1.70 (each bs, each 3H, —C=CCH$_3$), 1.87 (d, J=1.3 Hz, 3H, —C=CCH$_3$), 1.9-2.2 (m, 8H, —CH$_2$CH$_2$—), 2.89 (hep, J=7.0 Hz, 1H, —CH(CH$_3$)$_2$), 3.98 (bs, 2H$_2$, —CH$_2$Cl), 5.09 (m, 1H, —C=CHC H$_2$—), 5.47 (bt, J=6.5 Hz, 1H, —C=CHCH$_2$—), 6.82 (d, J=12.0 Hz, 1H, —C=CH—CH=C(CHO)—), 7.11 (d, J=12.0 Hz, —C=CH—CH=C(CHO)—), 10.27 (s, 1H, —CHO).

REFERENCE EXAMPLE 3

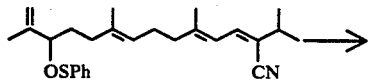

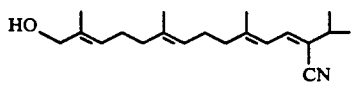

A solution of the sulfoxide (70.3 mg, 0.17 mmol) and trimethylphosphite (43 mg, 0.35 mmol) in methanol (0.5 ml) was allowed to stand at room temperature for 3 days in argon atmosphere. The methanol was evaporated under reduced pressure, and the residue was chromatographed on a column of silica gel eluting with n-hexane:ethyl acetate (6:1) to give the objective alcohol (37.1 mg, 72%).

IR (film) cm$^{-1}$; 3450, 2975, 2930, 2880, 2210, 1635, 1445, 1385, 1220, 1020.

NMR (CDCl$_3$, 250 MHz) δppm; 1.17 (d, J=6.7 Hz, 6H, CH(CH$_3$)$_2$), 1.62, 1.67 (each bs, each 3H, —C=CCH$_3$), 1.84 (d, J=1.2 Hz, 3H, —C=CCH$_3$), 2.0-2.2 (m, 8H, —CH$_2$CH$_2$—x 2), 2.53 (hep, J=6.7 Hz, 1H, —CH(CH$_3$)$_2$, 3.99 (bs, 2H, —CH$_2$OH), 5.11 (m, 1H, —CHCH$_2$—), 5.39 (bt, J=5.5 Hz, 1H, —CHCH$_2$—), 6.28, 6.83 (each d, J=11.5 Hz, each 1H, =CH—CH=).

REFERENCE EXAMPLE 4

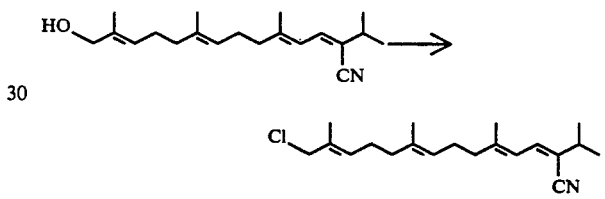

To a solution of the alcohol (904 mg, 3.0 mmol) in carbon tetrachloride (2 ml) was added triphenylphosphine (1.02 g, 3.9 mmol), and the resultant mixture was refluxed under heating for 1 hour. Most of the carbon tetrachloride was evaporated under reduced pressure, and the residue was mixed with n-hexane, filtered and washed. The filtrate was concentrated, and the residue was chromatographed on a column of silica gel eluting with hexane:ethyl acetate (10:1) as an eluent to give the objective chloride (890 mg, 93%).

IR (film)cm$^{-1}$; 2980, 2940, 2880, 2215, 1635, 1445, 1390, 1265, 1025.

NMR (CDCl$_3$, 250 MHz)δppm; 1.14 (d, J=6.8 Hz, 6H, CH(CH$_3$)$_2$), 1.59, 1.64 (each bs, each 3H, —C=CCH$_3$), 1.81 (d, J=1.0 Hz, 3H, —C=CCH$_3$), 1.9-2.2 (m, 8H, —CH$_2$CH$_2$—x 2), 2.50 (hep, J=6.8 Hz, 1H, —CH(CH$_3$)$_2$), 3.96 (bs, 2H, —CH$_2$OH), 5.08 (m, 1H, —CHCH$_2$—), 5.36 (bt, J=5.5 Hz, 1H, =CHCHz—), 6.25, 6.80 (each d, J=11.5 Hz, each 1H, =CH—CH=).

REFERENCE EXAMPLE 5

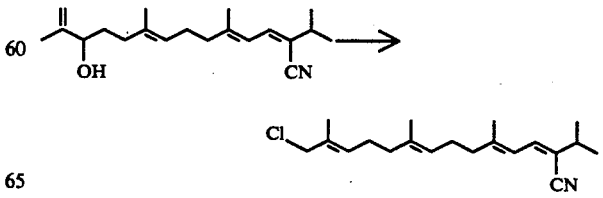

To a solution of the allyl alcohol (117 mg, 0.39 mmol) in diethyl ether (10 ml) was added thionyl chloride (0.029 ml, 0.40 mmol) on an ice water bath with stirring. Three hours later, the solvent was evaporated under reduced pressure, and the residue was chromatographed on a column of silica gel eluting with n-hexane:ethyl acetate (10:1) to give the chlorine compound (112 mg, 90%).

REFERENCE EXAMPLE 6

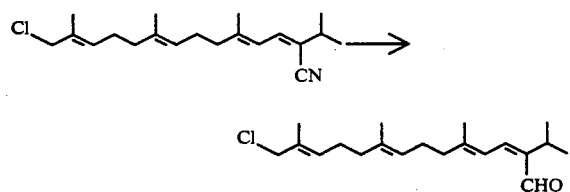

To a solution of the nitrile (890 mg, 2.78 mmol) in n-hexane (30 ml) was dropwise added gradually a 1M solution (4.2 ml) of diisobutylaluminum hydride in toluene at −70° C. under argon atmosphere. One hour later, 2 ml of water was added to the mixture, and the bath was removed. The reaction mixture was vigorously stirred, and the resultant solid was filtered and washed with n-hexane. The resultant filtrate was stirred still with 10% oxalic acid. The organic layer was washed, dried, filtered and concentrated. The residue was chromatographed on a column of silica gel eluting with n-hexane:ethyl acetate (20:1) to give the objective Compound F (781 mg, 87%).

REFERENCE EXAMPLE 7

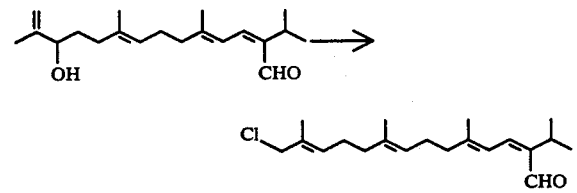

To a solution of the aldehyde obtained in Reference Example 4 (333 mg, 1.1 mmol) and propylene oxide (160 mg, 2.8 mmol) in ethyl ether (22 ml) was added thionyl chloride (157 mg, 1.3 mmol) with stirring under cooling. The reaction mixture was allowed to stand at room temperature for 8 hours, and the solvent was evaporated. The residue was chromatographed on a column of silica gel eluting with n-hexane:ethyl acetate (15:1) to give the objective Compound F (291 mg, 82%).

REFERENCE EXAMPLE 8

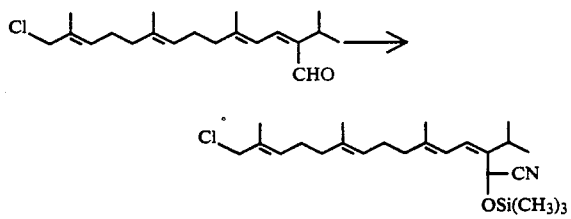

To a solution of Compound F (640 mg, 2.0 mmol) in trimethylsilylnitrile (0.35 ml, 2.6 mmol) was added a very amount of potassium cyanide/18 crown 6 ether complex on an ice water bath under nitrogen atmosphere. Two hour later, the starting material was confirmed to disappear, and the excessive trimethylsilylnitrile was evaporated to give the crude product (647 mg, quantitative yield).

IR (film)cm$^{-1}$; 2960, 2930, 2880, 2320, 1445, 1255, 1080, 875, 845.

NMR (CDCl$_3$, 250 MHz) δ ppm; 1.11, 1.15 (each d, J=6.9 Hz, each 3H, —CH(CH$_3$)$_2$), 1.60, 1.71, 1.77 (each s, each 3H, —C═CCH$_3$), 1.9-2.2 (m, 8H, —CH$_2$CH$_2$—), 2.64 (hep, J=6.9 Hz, 1H, —CH(CH$_3$)$_2$), 3.99 (s, 1H, —CH$_2$Cl), 5.11 (m, 1H, —C═CHCH$_2$—), 5.33 (s, 1H, —CHCN), 5.48 (bt, J=6.5 Hz, 1H, —C═CHCH$_2$—), 6.04, 6.25 (each d, J=11.3 Hz, each 1H, ═CH—CH═).

REFERENCE EXAMPLE 9

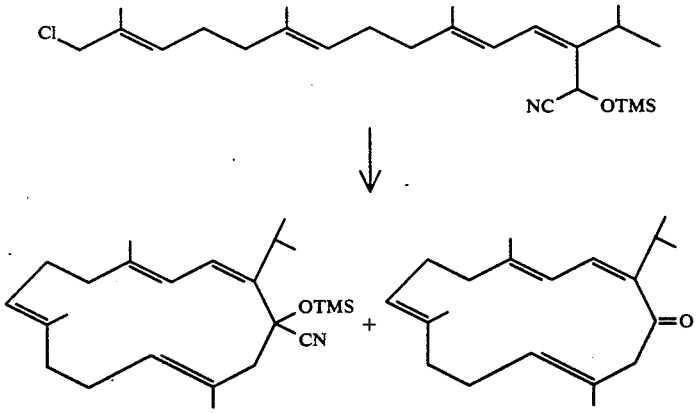

A 0.25M solution of lithium bis(trimethylsilyl) amide in tetrahydrofuran (20 ml, 5.0 mmol) was stirred on a 55° C. oil bath under argon atmosphere, and a solution of the starting material (378 mg, 0.895 mmol) in tetrahydrofuran (15 ml) was added dropwise over a period of 50 minutes to the solution. The resultant mixture was stirred at the same temperature for 20 minutes, and the reaction mixture was poured into a mixture of saturated brine (30 ml) and n-hexane (20 ml) containing 50 g of ice for stopping the reaction. The organic layer was separated and extracted with n-hexane and ether (5:1, 30 ml). The extract was dried over sodium sulfate, and the solvent was evaporated under reduced pressure. The resultant residue was chromatographed on a column of silica gel to give the cyclic product (288 mg, 83%) and the cyclic ketone (42.9 mg, 0.11 mmol, 16%).

The cyclic product had the following physical data.

IR (film) cm$^{-1}$; 2970, 2920, 1440, 1385, 1253, 1125, 1085, 940, 845, 755.

NMR (CDCl$_2$, 250 MHz) δ ppm; 0.23 (s, 9H, —SiMe$_3$), 1.09 1.15 (each d, J=6.7 Hz, each 3H, —CH(CH$_3$)$_2$), 1.50, 1.62 (each bs, each 3H, —C=CCH$_3$), 1.70 (d, J=1.3 Hz, 3H, —C=CCH$_3$), 2.0-2.2 (m, 8H, —CH$_2$CH$_2$×2), 2.51 (hep, J=6.7 Hz, 1H, —CH(CH$_3$)$_2$), 2.55, 2.65 (each d, J=14.2 Hz, each 1H, —CH$_a$H$_b$CN—), 4.94 (bt, J=6.1 Hz, 1H, —C=CHCH$_2$—), 5.15 (bt, J=5.6 Hz, 1H, —C=CHCH$_2$—), 6.17, 6.44 (each d, J=11.8 Hz, each 1H, =CH—CH=).

REFERENCE EXAMPLE 10

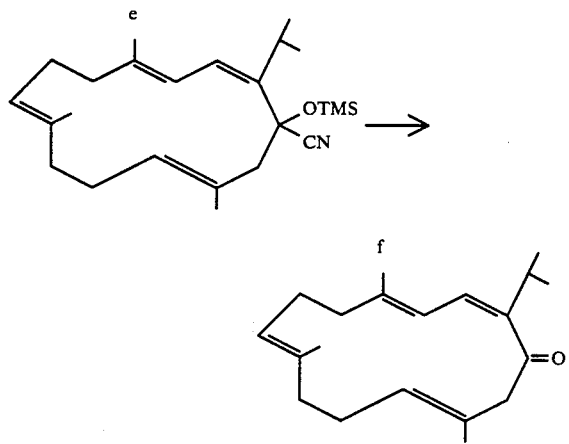

To a solution of the starting material (288 mg, 0.74 mmol) in tetrahydrofuran (10 ml) were added water (0.3 ml) and a 0.1M solution of tetrabutylammonium fluoride in tetrahydrofuran (16 μl, 0.016 mmol). The reaction mixture was stirred at room temperature for 17 hours, mixed with saturated brine (10 ml) and the organic product was extracted with n-hexane and ether (5:1, 30 ml×). The extract was dried over sodium sulfate and the solvent was evaporated under reduced pressure to give the cyclized ketone (200 mg, 94%).

REFERENCE EXAMPLE 11

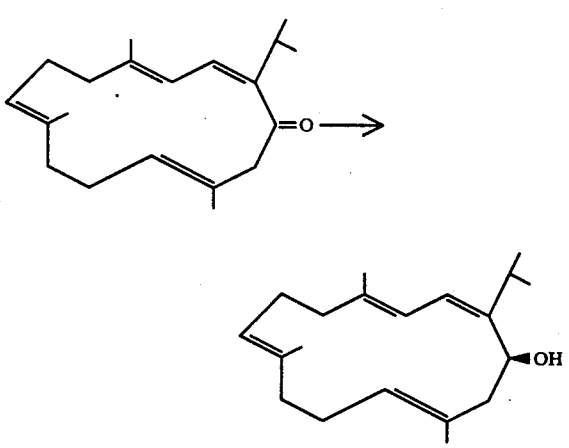

A solution of lithium aluminum hydride in diethyl ether (2.94 ml, 2.0 mmol, 0.68M) was stirred under argon atmosphere, and (S)-2-(2, 6-xylidinomethyl) pyrrolidine (490 mg, 2.4 mmol) was dropwise added gradually to the solution, which was stirred at room temperature for 2 hours. The reaction mixture was chilled at −74° C., and a solution of the macrocyclic ketone (69 mg, 0.24 mmol) in diethyl ether (3 ml) was dropwise added over a period of 10 minutes. The resultant mixture was stirred at −74° C. for 1 hour, mixed with saturated aqueous sodium sulfate (1 ml) and stirred at room temperature for some while. The reaction mixture was mixed with diethyl ether (10 ml) and dilute hydrochloric acid (20 ml), and the organic layer was separated. The aqueous layer was extracted with diethyl ether (20 ml), and the extract was washed with saturated brine (20 ml), dried over anhydrous sodium sulfate and concentrated under reduced pressure. The residue was chromatographed on a column of silica gel for purification to give the optically active sarcophytol A (61 mg, 88%).

The resultant optically active sarcophytol A was found to have an optical purity of 93% e.e. by chiral HPLC analysis.

$[\alpha]_D^{24}$: +204.4° (c=0.27, CHCl$_3$)

What is claimed is:

1. An acyclic terpene of the formula:

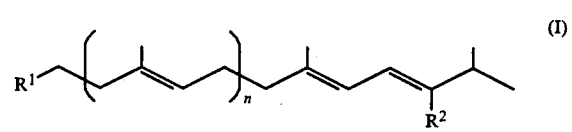

wherein R$^1$ is

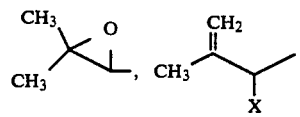

(X is a hydroxy group, chlorine atom, —OC(O)R$^3$ (R$^3$ is a hydrogen atom, C$_1$-C$_4$ alkyl or optionally substituted phenyl group), —SR$^4$, —S(O)R$^4$ (R$^4$ is a C$_1$-C$_4$ alkyl group or optionally substituted phenyl group), —NR$^5$R$^6$, or —N(O)R$^5$R$^6$ (R$^5$ and R$^6$ are independently a C$_1$-C$_4$ alkyl group or taken together form an alkylene ring)),

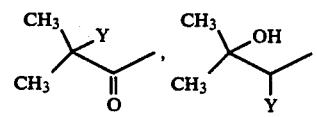

(Y is a halogen atom),

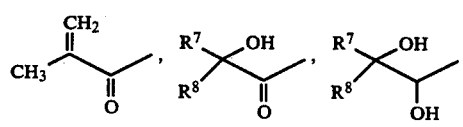

(R$^7$ and R$^8$ are independently a C$_1$-C$_4$ alkyl group or taken together from an alkylene ring),

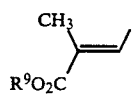
($R^9$ is a $C_1$–$C_4$ alkyl group),
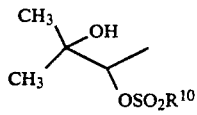
($R^{10}$ is a $C_1$–$C_4$ alkyl group optionally substituted by a halogen atom or an optionally substituted phenyl group), or a formyl group; $R^2$ is a cyano group, formyl group or $CO_2R^{11}$ ($R^{11}$ is a $C_1$–$C_4$ alkyl group); and n is 0 or 1, with the proviso that when n is 0, $R^1$ must be
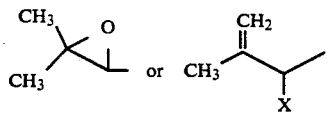
in which X is a hydroxy group, chlorine atom or —OC(O)$R^3$.
* * * * *